United States Patent [19]
Ross et al.

[11] Patent Number: 5,840,574
[45] Date of Patent: Nov. 24, 1998

[54] VIRAL VACCINES

[75] Inventors: Louis Joseph Norman Ross, Newbury, England; Simon David Scott, Amsterdam, Netherlands; Matthew McKinley Binns, Ely, United Kingdom

[73] Assignee: Rhône Mérieux, Lyons, France

[21] Appl. No.: 462,591

[22] Filed: Jun. 5, 1995

Related U.S. Application Data

[60] Division of Ser. No. 81,932, Jun. 23, 1993, Pat. No. 5,558,860, which is a continuation-in-part of Ser. No. 669,392, Apr. 29, 1991, abandoned.

[30] Foreign Application Priority Data

Sep. 13, 1988 [GB] United Kingdom ............... 8821441
Sep. 13, 1989 [WO] WIPO ............... PCT/GB89/01076

[51] Int. Cl.$^6$ ............... C12N 15/85; C12N 15/38
[52] U.S. Cl. ............... 435/320.1; 536/23.72
[58] Field of Search ............... 435/320.1, 235.1, 435/172.3; 536/23.5, 23.72

[56] References Cited

PUBLICATIONS

Buckmaster et al., "Gene Sequence and Mapping Data from Marek's Disease Virus and Herpesvirus of Turkeys: Implications for Herpesvirus Classification", J.gen.Virol. (1988) 69, 2033–2042.

Fukuchi et al., "Structure of Marek's Disease Virus DNA: Detailed Restriction Enzyme Map", Journal of Virology, Jul. 1984, pp. 102–109, vol. 51, No. 1.

Ono et al., "Partial Protection against Marek's Disease in Chickens Immunized with Glycoprotens gB Purified from Turkey–Herpesvirus–Infected Cells", Avian Diseases, vol. 29, No. 2, pp. 533–539.

Sithole et al., "Identification of Marek's Disease Herpes–Virus B Antigen Precursor Polypeptide and the Gene Encoding It", 13th International Herpes Workshop, California, Jul. 13, 1988, p. 221.

Brunovskis et al., "Identification of Genes Mapping in the Marek's Disease Herpesvirus Unique Short Region", 13th International Herpes Workshop, California, Jul. 13, 1988, p. 222.

Kato et al., "Advances in Marek's Disease Research", Proceedings of the 3rd International Symposium on Marek's Disease, Sep. 12–16, 1988.

Ikuta et al., "Immunoprecipitation of Marek's Disease Virus–Specific Polypeptides with Chicken Antibodies Purified by Affinity Chromatography", Virology 114, 227–281 (1981).

Igarashi et al., "Restriction Enzyme Map of Herpevirus of Turkey DNA and Its Collinear Relationship with Marek's Disease Virus DNA", Virology 157, 351–358 (1987).

Silva et al., "Monoclonal Antibody–Mediated Immunoprecipitation of Proteins from Cells Infected with Marek's Disease Virus or Turkey Herpes–Virus", Virology 136, 307–320 (1984).

Silva et al., Isolation and Partial Characterization of Three Glyco–proteins Common to Marek's Disease Virus and Turkey Herpesvirus–Infected Cells, pp. 101–110, Int'l Symposium on Marek's Disease, Ithaca, New York.

Gibbs et al., "Extensive Homology Exists Between Marek's Disease Herpesvirus and Its Vaccine Virus, Herpesvirus of Turkeys", Proc.Natl. Acad. Sci., vol. 81, pp. 365–3369, Jun. 1984.

Schat, Cancer Surveys, vol. 6, 1987, pp. 1–37.

*Primary Examiner*—James Ketter
*Attorney, Agent, or Firm*—Larson & Taylor

[57] ABSTRACT

A vaccine effective against Marek's disease virus (MDV) comprises (a) an MDV attenuated by virtue of being TK– or (b) a host expressing an MDV antigen, namely the respective MDV homologues of the HSV gB, gC, gD or gH glycoproteins (or antigenic parts thereof) or the respective MDV homologues of the HSV-1 immediate early genes IE-68 or IE-175. The host may be a herpes virus of turkeys (HVT), more particularly HVT in which the MDV antigen is inserted in the HVT homologue of the HSV gC gene, the ribonucleotide reductase (large subunit) gene or the thymidine kinase (TK) gene.

**4 Claims, 66

```
TCGAGCTCGCCCGGGGATGTTTAGTCACGATAGACATCGGT
         10        20        30        40

TCGCCCAGCCGTCGAATACAGCATTATATTTTAGTGTTG
         50        60        70        80

AAAATGTAGGGCTGCTTCCTCACTTAAAGGAGGAAATGGCT
         90       100       110       120

CGATTCATGTTTCATAGCAGTAGAAAAACAGATTGGACCG
        130       140       150       160

TCAGTAAGTTTAGAGGGTTTTATGACTTTAGCACTATAGA
        170       180       190       200

TAATGTAACTGCGGCCCATCGCATGGCTTGGAAATATATC
        210       220       230       240

AAAGAACTGATTTTTGCAACAGCTTTATTTTCTTCTGTAT
        250       260       270       280

TTAAAATGTGGCGAATTGCACATCTGTCGTGCCGACAGTTT
        290       300       310       320

GCAGATCAACAGCAATGGAGACTATGTATGGAAAAATGGA
        330       340       350       360
```

FIG. 2A

ATATATATAACATATGAAACCGAATATCCACTTATAATGA
         370              380             390           400
TTCTGGGGTCAGAATCAAGCACTTCAGAAACGCAAAATAT
         410              420             430           440
GACTGCAATTATTGATACAGATGTTTTTCGTTGCTTTTAT
         450              460             470           480
TCTATTTTGCAGTATATGGCCCCCGTTACGGCAGATCAGG
         490              500             510           520
TGCGGAGTAGAACAGATTACCAACAGCCACGCCCCCATCTG
         530              540             550           560
ACCCGTCCAATATTCTTGTGTCCCCTGCATTTTATCTCACA
         570              580             590           600
                                              M   H
CAATTTATGAACAGCATCATTAAGATCATCTCACTATGCA
         610              620             630           640
 Y   F   R   N   C   I   F   F   L   I   V   I
CTATTTTAGGCGGAATTGCATTTTTTCCTTATAGTTATT
         650              660             670           680

FIG. 2B

```
L Y G T N S S P S T Q N V T
CTATATGGTACGAACTCATCTCCGAGTACCCAAAATGTGA
        690       700       710       720

S R E V V S S V Q L S E E
CATCAAGAGAAGTTGTTTCGAGCGTCCAGTGTCTGAGGA
        730       740       750       760

E S T F Y L C P P P V G S
AGAGTCTACGTTTTATCTTTGTCCCCACCAGTGGGTTCA
        770       780       790       800

T V I R L E P P R K C P E P
ACCGTGATCCGTCTAGAACCGCCGAAAATGTCCCGAAC
        810       820       830       840

R K A T E W G E G I A I L
CTAGAAAAGCCACCGAGTGGGGTGAAGGAATCGCGATATTA
        850       860       870       880
```

FIG. 2C

```
       F   K   E   N   I   S   P   Y   K   F   K   V   T
       TTTAAAGAGAATATCAGTCCATATAAATTTAAAGTGACGC
       GAGAATATCAGTCCGTATAAATTCAAAGTAACAC
                 890       900       910       920

L   Y   Y   K   N   I   I   Q   T   T   T   W   T   G
                                    -V-
       TTTATTATAAAAATATCATTCAGACGACGACATGGACGG
       TTTACTATAAGAACGTTATACAAACTACGACGTGGACTG
                 930       940       950       960

T   T   Y   R   Q   I   T   N   R   Y   T   D   R
       GGACGACATAGACAGATCACTAATCGATATACAGATAG
       GGACGACGTACAGACAGATAACTAACAGGTATACAGATAG
                 970       980       990       1000
```

FIG. 2D

```
                    ---D---|
         T  P  V  S  I  E  E  I  T  D  L  I  D
         GACGCCCGTTTCCATTGAAGAGATCACGGATCTAATCGAC
            ||| ||||||  ||||  ||||  || ||| ||
         AACACCCGTGTCTATCGACGAAATTACTGATTTGATAGAT
         1010       1020       1030       1040

---------K-------|           -------Y  R  N
         G  K  G  R  C  S  S  K  A  R  Y  L  R  N
         GGCAAAGGAAGATGCTCATCTAAAGCAAGATACCTTAGAA
           |||| |||||  ||||  || |||    ||   ||
         GGTAAGGGGAAATGTTCATCCAAAGCCCGGTATCTTTCG
         1050       1060       1070       1080

N  V  Y  V  E  A  F  D  R  D  A  G  E
         ACAATGTATATGTTGAAGCGTTTGACAGGGATGCGGGAGAA
         1090       1100       1110       1120

K  Q  V  L  L  K  P  S  K  F  N  T  P
         AAACAAGTACTTCTAAAACCATCAAAATTCAACACGCCCC
         1130       1140       1150       1160
```

FIG. 2E

```
           E  S  R  A  W  H  T  T  N  E  T  Y  T  V
           GAATCTAGGGCATGGCACACGACTAATGAGACGTATACCG
           |||||||||||||||||||||||||||||||||||||||
           GGCATGGCATACGACCAACGAGACGTACACCG
                    1170     1180     1190     1200

----------V----------
           W  G  S  P  W  I  Y  R  T  G  T  S  V
           TGTGGGGATCACCATGGATATATCGAACGGGAACCTCCGT
           ||||||||||||||||||||||||||||||||||||||||
           TGTGGGGATCTCCATGGTATATAGAACGGGCACGTCCGT
                1210     1220     1230     1240

-------A----
           N  C  I  V  E  E  M  D  A  R  S  V  F
           CAATTGTATAGTAGAGGAAATGGATGCCCGCTCTGTGTTT
           ||||||||||||||||||||||||||||||||||||||||
           CAACTGCATAGTAGAAGAGATGGATGCCAGATCAGCATTT
                1250     1260     1270     1280
```

FIG. 2F

```
---T---|----|----|----|----|----|----|----|----|----|---|---|---|----N
   P  Y  S  Y  F  A  M  A  N  G  D  I  A  N
CCGTATTCATATTTGCAATGGCCAATGGGCGACATCGCGA
|||||||||||||||||||||||||||||||||||||||
CCATACACGTACTTTGCAATGGCCAATGGAGATATCGCAA
          1290       1300       1310       1320

---M---|----|----|---T--|---T--|---T--D-|----|----|----|----A
   I  S  P  F  Y  G  L  S  P  P  E  A  A
ACATATCTCCATTTTATGGTCTATCCCACCAGAGGCTGC
|||||||||||||||||||||||||||||||||||||||
ACATGTCTCCATTTTATGGAACAACTCCAACGACGCCGC
          1330       1340       1350       1360

----|----|----|---S---|----|---R---|---R---|----|----Q
   A  E  P  M  G  Y  P  Q  D  N  F  K  Q
CGCAGAACCCATGGGATATCCCCAGGATAATTTCAAACAA
|||||||||||||||||||||||||||||||||||||||
CGCGGAGCCCATGAGCTATCCGCAAGACCGATTCAGGCAA
          1370       1380       1390       1400
```

*FIG. 2G*

```
 -F---------------P-------------T-----
  L  D  S  Y  F  S  M  D  L  D  K  R  R  K
 CTAGATAGCTATTTTCAATGGATTTGGACAAGCGTCGAA
 |   ||||||||||||||||||  ||||||  |||||||
 TTTGACAGCTATTTCCCATGGATTTGGATACGCGCCGAA
         1410         1420        1430        1440

A  S  L  P  V  K  R  N  F  L  I  T  S
 AAGCAAGCCCTTCCAGTCAAGCGTAACTTTCTCATCACATC
 ||
 AA
         1450        1460        1470        1480

H  F  T  V  G  W  D  W  A  P  K  T  T
 ACACTTCACAGTTGGGTGGGACTGGGCTCCAAAAACTACT
         1490        1500        1510        1520

R  V  C  S  M  T  K  W  K  E  V  T  E  M
 CGTGTATGTTCAATGACTAAGTGGAAAGAGGTGACTGAAA
         1530        1540        1550        1560

L  R  A  T  V  N  G  R  Y  R  F  M  A
 TGTTGCGTGCAACAGTTAATGGGAGATACAGATTTATGGC
         1570        1580        1590        1600
```

FIG. 2H

```
R  E  L  S  A  T  F  I  S  N  T  T  E
CCGTGAACTTTCGGCAACGTTTATCAGTAATACGACTGAG
     1610          1620         1630         1640

F  D  P  N  R  I  I  L  G  Q  C  I  K  R
TTTGATCCAAATCGCATCATATTAGGACAATGTATTAAAC
     1650         1660         1670         1680

E  A  E  A  A  I  E  Q  I  F  R  T  K
GCGAGGCAAGAAGCAGCAATCGAGACAGATATTTAGGACAAA
     1690         1700         1710         1720

Y  N  D  S  H  V  K  V  G  H  V  Q  Y
ATATAATGACAGTCACGTCAAGGTTGGACATGTACAATA
     1730         1740         1750         1760

F  L  A  L  G  G  F  I  V  A  Y  Q  P  V
TTTCTTGGCTCTCGGGGATTTATTGTAGCATATCAGCCTG
     1770         1780         1790         1800

L  S  K  S  L  A  H  M  Y  L  R  E  L
TTCTATCCAAATCCCTGGCTCATATGTACCTTCAGAGAATT
     1810         1820         1830         1840
```

FIG. 2I

```
            M  R  D  N  R  T  D  E  M  L  D  L  V
          GATGAGAGACAACAGGACCGATGAGATGCTCGACCTGGTA
            1850        1860        1870        1880

N  N  K  H  A  I  Y  K  K  N  A  T  S  L
          AACAATAAGCATGCAATTTATAAGAAAAATGCTACCTCAT
            1890        1900        1910        1920

S  R  L  R  R  D  I  R  N  A  P  N  R
          TGTCACGATTGCGGGCGAGATATTCGAAATGCACCAAATAG
            1930        1940        1950        1960

K  I  T  L  D  D  T  T  A  I  K  S  T
          AAAAATAACATTAGACGACACCACAGCTATTAAATCGACA
            1970        1980        1990        2000

S  S  V  Q  F  A  M  L  Q  F  L  Y  D  H
          TCGTCTGTTCAATTCGCCATGCTCCAATTTCTTTATGATC
            2010        2020        2030        2040

I  Q  T  H  I  N  D  M  F  S  R  I  A
          ATATACAAACCCATATTAATGATATGTTTAGTAGGATTGC
            2050        2060        2070        2080
```

*FIG. 2J*

```
T  A  W  C  E  L  Q  N  R  E  L  V  L
CACAGCTTGGTGCGAATTGCAGAATAGAGAACTTGTTTTA
        2090         2100        2110        2120

W  H  E  G  I  K  I  N  P  S  A  T  A  S
TGGCACGAAGGGATAAAGATTAATCCTAGCGCTACAGCGA
        2130        2140        2150        2160

A  K  M  L  G
                                      CAAAGATGTTGGG
                                      || ||||||||||
                                      GCCAAAATGTTGGG
                                            2190        2200
A  T  L  G  R  R  V  A
GTGCAACATTAGGAAGGAGAGTGGCTGCAAAGATGTTGGG
        2170        2180        2190        2200

-----D-------------------I--E--T-----S-
D  V  A  A  V  S  S  C  T  A  I  D  A
GGATGTCGCTGCTGTATCGAGCTGCACTGCTATAGATGCG
        2210        2220        2230
TGACGATGCCGCCGTATCATCATGTATTGAGACTGATTCA
        2210        2220        2230        2240
```

FIG. 2K

```
    -D------------------------V----
     E  S  V  T  L  Q  N  S  M  R  V  I  T  S
    GAATCCGTCACTTGCAAAATTCTATGCGAGTTATCACAT
    ||||||||||||||||||||||||||||||||||||||
    GATTCTGTTACCTTACAAAATTCCATGCGGGTTGTCACCT
            2250         2260         2270         2280

T  N  T  C  Y  S  R  P  L  V  L  F  S
    CCACTAATACATGTTATAGCCGACCATTGGTTCTATTTC
    ||||||||||||||||||||||||||||||||||||||
    CTACCAATACTTGTTATAGCCGCCCTTTAGTGTTATTCTC
            2290         2300         2310         2320

------D--R-----D--K---
     Y  G  E  N  Q  G  N  I  Q  G  Q  L  G
    ATATGGAGAAAACCAAGGAAACATACAGGACAACTCGGTG
    ||||||||||||||||||||||||||||||||||||||
    CTACGGGACCGACAAGACAAAATACAAGGACAGTTGGGGG
            2330         2340         2350         2360
```

FIG. 2L

```
E  N  N  E  L  L  P  T  L  E  A  V  E  P
AAAACAACGAGTTGCTTCCAACGCTAGAGGCTGTAGAGC
|||||||||||||||||||||||||||||||||||||||
AAAACAATGAATTGATTCCAACTCTAGAGGCCATAGAGC
         2370      2380      2390      2400

C  S  A  N  H  R  R  Y  F  L  F  G  S
         CATGCTCGGCTAATCATCGTAGATATTTTCTGTTTGGATC
         |||||||||||||||||||||||||||||||||||||||
         CATGTTCGGCCAATCATCATCGTAGA
              2410      2420      2430      2440

G  Y  A  L  F  E  N  Y  N  F  V  K  M
CGGTTATGCTTTATTTGAAAACTATAATTTTGTTAAGATGG
           2450      2460      2470      2480

V  D  A  A  D  I  Q  I  A  S  T  F  V  E
TAGACGCTGCCGATATACAGATTGCTAGCACATTTGTCG
           2490      2500      2510      2520
```

FIG. 2M

```
      L   N   L   T   L   L   E   D   R   E   I   L   P
    AGCTTAATCTAACCCTGCTAGAAGATCGGGAAATTTTGCC
        2530            2540            2550            2560

L   S   V   Y   T   K   E   E   L   R   D   V   G
    TTTATCCGTTTACACAAAAGAAGAGTTGCGTGATGTTGGT
        2570            2580            2590            2600

V   L   D   Y   A   E   V   A   R   R   N   Q   L   H
    GTATTGGATTATGCAGAAGTAGCTCGCCGCAATCAACTAC
        2610            2620            2630            2640

E   L   K   F   Y   D   I   N   K   V   I   E   V
    ATGAACTTAAATTTTATGACATAAACAAAGTAATAGAAGT
        2650            2660            2670            2680

D   T   N   Y   A   F   M   N   G   L   A   E   L
    GGATACAAATTACGCGTTTATGAACGGTTTGGCCGAATTG
        2690            2700            2710            2720

F   N   G   M   G   Q   V   G   Q   A   I   G   K   V
    TTTAACGGTATGGGTCAGGTCAAGCTATAGGCAAAG
        2730            2740            2750            2760
```

FIG. 2N

```
      V  V  G  A  A  G  A  I  V  S  T  I  S
TTGTAGTAGGGGCTGCCGGTGCAATCGTATCTACCATATC
      2770          2780          2790          2800

G  V  S  A  F  M  S  I  P  L  G  L  S
TGGTGTCTCTGCTTTCATGTCAATCCCCTTTGGGCTTTCG
      2810          2820          2830          2840

A  I  G  L  I  I  A  G  L  V  A  A  F
GCAATCGGTTTAATCATTATAGCAGGACTCGTGGCTGCAT
      2850          2860          2870          2880

L  A  Y  R  Y  V  N  K  L  K  S  N  P
TTTTAGCATATCGTTATGTAAACAAGCTTAAAAGCAATCC
      2890          2900          2910          2920

M  K  A  L  Y  P  M  T  T  E  V  L  K
AATGAAAGCCCTTTATCCTATGACAACAGAAGTGCTTAAG
      2930          2940          2950          2960

A  Q  A  T  R  E  L  H  G  E  E  S  D  D
GCACAGGCAACGCGTGAGTTGCATGGCGAGGAATCAGATG
      2970          2980          2990          3000
```

*FIG. 20*

```
   L   E   R   T   S   I   D   E   R   K   L   E   E
ATTTGGAACGAACACATCTATTGATGAAAGAAAATTAGAAGA
           3010              3020              3030              3040

A   R   E   M   I   K   Y   M   A   L   V   S   A
AGCTAGAGAAATGATAAAATATATGGCGTTAGTCTCCCGCG
           3050              3060              3070              3080

E   E   R   H   E   K   K   L   R   K   R   R   G
GAAGAACGCCACGAGAAAAACTGCGGAGAAAGAGGCGAG
           3090              3100              3110              3120

T   T   A   V   L   S   D   H   L   A   K   M   R
GCACTACCGCCGTTCTATCGGACCACCTGGCAAAAATGAG
           3130              3140              3150              3160

I   K   N   S   N   P   K   Y   D   K   L   P   T
GATTAAAAATAGTAACCCTAAATATGATAAGTTACCTACT
           3170              3180              3190              3200

T   Y   S   D   S   E   D   D   A   V   *
ACATATTCAGACTCAGAAGATGATGCTGTGTAAGTGGGCA
           3210              3220              3230              3240

CTATTATATTTGAACTGAATAAAAACGCCATAGAGCATGATA
           3250              3260              3270              3280
```

FIG. 2P

```
TGGTTTACTCATTTATTGCGAGATATAAAGCATATTCAAT
     3290           3300          3310          3320

ACGATATATTGCGAACGTGATGCTAAAAACATAGCTCCCT
     3330           3340          3350          3360

GTATTATTGATGCGCCATCATTTGATTAATAAATACATCG
     3370           3380          3390          3400

ACGCCGGCATCACTGGTGCGGTGTATACCAGCTACGGCGC
     3410           3420          3430          3440

TAGCATTCATGGTATCCCCGTGATTGCTCGATGCTTTCCTT
     3450           3460          3470          3480

CTGAATTCCGTCGGAACGCTCCTGAGAGATGGTCGCAGTT
     3490           3500          3510          3520

ATTGGTACATTTCGACCAGCCCGGATCTGAAACTGGCA
     3530           3540          3550          3560

CAGGAATGCACCGTGGAATTGGTAGAAGTTTTTCCTTCCG
     3570           3580          3590          3600
```

FIG. 2Q

TGGAAGGCATAGGGCGTTCGACTCCCATGGGCCATGAAACTGTGGGATGT
         3610      3620      3630      3640      3650

*FIG. 2R*

```
TATTATTGGTCCATGCTAGAATAGTCATACGCTACGATCT
         10        20        30        40
GTTGCTATATATGACTATCGCCAAACTGTTAAACCCGCGA
         50        60        70        80
AGAATATATTTCATATAAACCTAAGGGCCCCTCAGTCTGA
         90       100       110       120
                                 M  K  F  Y  C  L
TTTTTTGTGAAAACGTGTATACCATGAAGTTTTACTGCCT
        130       140       150       160
 I  R  F  M  I  I  A  N  L  Y  S  S  Y
AATCCGTTTCATGATCATAGCGAATCTTTATTCATCTTAC
        170       180       190       200
 Q  I  S  L  P  G  T  Y  P  S  Q  I  L  L
CAAATATCGCTTCCAGGCACATATCCATCGCAAATATTGC
        210       220       230       240
 D  M  K  N  S  P  L  V  R  F  N  I  S
TTGACATGAAGAACTCGCCCGCTCGTACGCTTTAATATATC
        250       260       270       280
```

FIG. 4A

```
       T  R  D  Y  K  D  E  T  L  W  I  R  K
GACGGCGTGATTATAAAGACGAGACACTCTGGATACGGAAA
            290           300           310           320

N  S  T  F  V  Y  I  D  T  A  V  T  T  A
AATTCGACATTTGTTTATATCGATACGGCTGTGACGACAG
            330           340           350           360

N  V  I  F  Y  L  P  I  G  Q  V  R  Q
CGAACGTTATCTTTTATCTGCCGATCGGTCAGGTACGACA
            370           380           390           400

M  V  F  F  K  R  P  I  S  R  L  L  T
AATGGTTTTTTCAAGCGTCCAATATCCAGGCTACTAACG
            410           420           430           440

S  N  N  L  V  K  F  I  N  T  G  S  Y  A
TCCAATAACCTGGTTAAATTTATTAATACCGGTTCATACG
            450           460           470           480

N  H  F  K  T  E  L  S  P  Y  L  S
CCAATCATACATTCAAGACAGAACTTTCACCCTATTTGTC
            490           500           510           520
```

FIG. 4B

```
K   T   N   T   P   L   K   K   Y   E   I   V   V
GAAAACCAATACACCCGTTGAAGAAATATGAAATTGTTGTC
         530             540             550             560

D   Q   P   T   G   E   N   P   P   A   G   F   G   S
GATCAACCTACTGGAGAAAACCCTCCGGCAGGGTTCGGAA
         570             580             590             600

L   K   P   A   D   F   L   N   P   G   Y   K   F
GTTTAAAACCGGCAGACTTTCTCAACCCCGGATACAAGTT
         610             620             630             640

V   L   T   S   E   L   V   G   A   Y   T   K   R
CGTTCTCACAAGCGAGTTGGTAGGAGCCTACACAAAACGA
         650             660             670             680

S   C   F   V   D   P   M   D   S   L   V   P   I   D
TCTTGTTTTGTCGATCCGATGGATTCTCTCGTCCCGATAG
         690             700             710             720

Y   D   H   V   R   T   I   I   F   G   S   A   G
ATTATGATCATGTACGAACCATTATATTCGGATCTGCTGG
         730             740             750             760
```

FIG. 4C

```
M  E  I  L  M  K  M  G  I  T  L  A  S
GATGGAGATTTTAATGAAGATGGGAATTACTTTGGCATCT
        770       780       790       800

M  T  I  S  T  K  Y  N  P  P  I  E  L  I
ATGACCATTTCGACGAAATATAATCCTCCTATTGAACTGA
      810       820       830       840

I  S  A  K  Y  R  N  L  S  L  L  W  P
TAATATCTGCAAAGTACCGAAATTTATCACTGTTGTGGCC
        850       860       870       880

P  R  Q  Q  Y  E  P  V  N  K  G  T  G
ACCCCGACAACAATATGAACCTGTAAATAAAGGGACTGGA
        890       900       910       920

R  P  H  W  I  Y  L  L  G  V  Y  R  N  V
CGCCCCCATTGGATCTACCTATTAGGTGTGTATAGAAACG
      930       940       950       960

S  D  S  E  R  D  S  Y  M  N  M  I  K
TTTCGGACTCCGAGCGTGACTCATACATGAATATGATTAA
        970       980       990       1000
```

FIG. 4D

```
  S   L   G   D   S   M   D   Y   H   F   L   I   S
GAGTCTGGGGCGATTCTATGGATTATCACTTCCTAATTAGC
         1010              1020              1030              1040

R   A   H   A   Q   M   L   I   L   A   A   E   D   R
AGAGGCCATGCCCAGATGCTGATACTGGCCAGCAGAGGACC
         1050              1060              1070              1080

L   V   D   E   M   H   S   F   R   N   V   I   A
GGCTCGTGGATGAAATGCATAGTTTCAGGAACGTTATTGC
         1090              1100              1110              1120

R   L   F   V   S   L   F   A   F   I   R   N   A
GCGTTTATTTGTATCGTTGTTCGCATTCATACGTAACGCA
         1130              1140              1150              1160

F   Q   S   G   Y   T   S   L   N   D   I   E   I
TTTCAGTCTGGCTACACCTCTCTTAATGACATAATTGAAA
         1170              1180              1190              1200

E   A   D   L   R   L   I   V   E   G   I   S   S
TCGAAGCCGATTTGAGGTTAATTGTAGAAGGCATTTCTTC
         1210              1220              1230              1240
```

*FIG. 4E*

```
     A   A   F   R   K   D   A   S   T   H   F   L   I
TGCTGCATTTCGTAAAGACGCTAGTACACACTTTCTTATA
         1250            1260           1270            1280

S   G   T   P   I   K   D   S   K   A   D   L   I   K
TCGGGAACGCCCATAAAAGATAGCAAAGCGGATTTAATTA
         1290            1300           1310            1320

S   L   L   S   K   V   I   R   P   I   S   G   H
AATCGTTGTTGTCTAAAGTCATTCGACCAATTTCCGGACA
         1330            1340           1350            1360

T   R   P   L   S   A   I   Q   H   L   F   L   L
TACACGTCCCTTATCTGCGATACAACATCTATTCCTTTTG
         1370            1380           1390            1400

R   S   A   Y   A   L   D   I   P   R   Q   N   G   S
AGATCCGCTTATGCATTGGATATACCCCGTCAAAACGGAT
         1410            1420           1430            1440

L   S   E   Q   V   S   T   V   A   L   S   F   I
CTTTGAGCAACAGGTATCTACAGTGGCACTGTCGTTCAT
         1450            1460           1470            1480
```

FIG. 4F

```
E   N   I   H   S   E   A   M   R   D   I   L   S
TGAAAAATATTCACAGGCCATGAGGGACATTCTGTCA
         1490            1500            1510            1520

W   N   T   T   K   H   A   L   Y   Y   A   F   A
TGGAACACTACAACAAAGCATGCCGTTGTATTATGCATTCG
         1530            1540            1550            1560

S   I   L   Q   R   P   L   T   E   W   G   A   S
CGAGTATTTTGCAACGGCCACTGACCGAATGGGGCGCCTC
         1570            1580            1590            1600

R   N   A   R   R   A   I   L   L   A   S   S   M
AAGAAATGCACGGAGGGCAATACTATTAGCATCATCGATG
         1610            1620            1630            1640

C   T   E   E   H   V   I   A   T   E   L   A   I   Q
TGTACAGAGAGCATGTTATCGCAACTGAGTTGGCTATTC
         1650            1660            1670            1680

E   L   Y   V   K   I   R   S   N   A   D   P   I
AAGAACTGTATGTCAAAATCAGAAGTAATGCCGACCCAAT
         1690            1700            1710            1720
```

FIG. 4G

```
         H  L  L  D  V  Y  T  P  C  L  S  S  L
         ACACCTTCTAGACGTATATACACCATGTCTTTCTTCACTA
             1730          1740          1750          1760

R  L  D  L  S  E  H  H  H  R  I  Y  A  M  A
         CGATTGGACCTTTCCGAACCACCATCGGATATACGGCAATGG
             1770          1780          1790          1800

D  V  V  F  Y  P  D  I  Q  Q  Y  L  K
         CAGATGTAGTTTTCTATCCAGACATTCAGCAGTATTTGAA
             1810          1820          1830          1840

K  K  S  H  E  G  N  M  K  E  D  D  L
         AAAAAATCCCATGAGGGTAATATGAAGGAAGATGATCTC
             1850          1860          1870          1880

E  T  K  A  E  Y  I  L  T  K  L
         GAAACAAAGGCGGAATACATCCTCACCAAGCTT
             1890          1900          1910
```

FIG. 4H

```
AAGCTTTTTGTAAAAACGATTATGACCACGGACACCCGCT
         10        20        30        40

TTTAGCAATCCTGCCATAAGGTGGTTTCCCGCGTGCTTGC
         50        60        70        80

CTCGAAGACAATTGCCAGCTAATCCAGCATTACCATATTT
         90       100       110       120

|----S---Q
              --M---T---S---A---Q-----I----
                              M   A   L   P
                           R   R   P   P   T   L   T   R   V   Y   L   D   G
CCTTGGCTTGCATTTGGATCTGCGCGTCGATGGCATIGCC  GAGAAGAGACCGCCCACGTTAACGCGAGTTTATCTAGACGGA
        130       140        150         ATGGCATCTCA
                                                     170       180       190       200
                                          GATGACATCTGCACAGCTCATACGTGTATACCTCGATGGA
```

FIG. 5A

```
-S--M-----------------------M-------E--I--
 P  F  G  I  G  K  T  S  I  L  N  A  M  P
CCGTTTGGTATAGGCAAAACGTCTATACTAAACGCTATGC
   ||||||||||||  |||||||||||||   |||| ||
TCAATGGGTATAGGTAAAACGTCAATGTTGAATGAGATAC
         210          220          230          240

---T-----L|
       D  H  T  P  D  G  A  P  I  L  K  V  Y
      CCGACCACACGCCCCGATGGGGCTCCTATATTGAAAGTGTA
      ||
      CGACATCTT
                250          260          270          280

E  P  M  K  Y  W  R  C  Q  S  T  D  L
     CGAACCAATGAAATATTGGAGATGCCAGTCTACCGATTTG
                290          300          310          320
```

FIG. 5B

```
                            -------R---
V  V  A  A  N  E  T  P  E  R  R  R  G  G
GTGGTAGCTGCCAACGAAACGCCAGAACGTAGGCGTGGTG
        |||||||||||||||||||||||||
        ATCGTCGTCGCAGGG
   330      340       350      360

---E---F----L------------S-------V--T--A
 A  L  S  G  F  Q  S  D  M  I  M  A  S
GAGCTTTATCACGATTCCAATCTGACATGATCATGGCATC
|||||| ||| |||||  |||||||| ||||| |||||
GAGAGTTTCTTTATTTCAATCTAGCATGATTGTAACAGC
   370      380       390      400

---L-----S--K------------------------V--
 I  Q  A  R  F  A  D  P  Y  L  L  F  H
TATACAAGCCAGATTTGCCGATCCATATTTGCTTTTTCAC
||||||||||| |||||||||||||| ||||| |||||||
TTTACAATCAAAGTTTGCAGATCCCTATCTTGTATTTCAT
   410      420       430      440
```

*FIG. 5C*

```
             ------H--R--I--T--G--T--R
      E  R  L  S  S  K  C  R  G  K  I  E  I  C
      GAACGGTTATCATCTAAATGTAGAGGAAAATAGAAATAT
         |||  ||||||  ||||||||  |||||  |||||||
      GAGCGGCTTATCGTCGAAGTGTCATCGCATAACAGGAACAC
               450         460         470         480

---G--N-----S--L-----I-----------H-----R--H--P
      D  T  P  A  I  I  L  M  L  D  R  H  P
      GCGATACTCCAGCAATTATATTAATGCTGGATAGGCACCC
        |||||||||  ||||||||||  |||||||  ||
      GTGGCAATCCATCGCTTATATTAATTCTAGATCGACATCC
               490         500         510         520

---I--S-----T--V-----------A-----H-----
      V  A  A  I  L  C  F  P  I  T  R  Y  L
      TGTGGCGGCGATATTATGTTTCCCAATCACTCGCTATTTA
        ||||||  |||  ||||||  |||||||||  ||||||
      CATATCCGCTACCGTATGTTTTCCCATTGCTCGACATTTA
               530         540         550         560
```

*FIG. 5D*

```
   -T----D--C-------------------------M-------------I
    L  G  E  Y  S  L  E  M  L  I  S  I
   CTTGGAGAATATTCTTTGGAAATGTTGATTAGCTCTATAA
   ||||||||||| || ||||||||| | ||||||||
   ACTGGAGATTGTTCCTTGAGAGATGCTAATTAGTATGATAA
            570            580            590            600

-------------Q--------P-------------------V--I
    R  L  P  L  E  S  P  G  C  N  L  T  V
   TAAGACTTCCGTTGGAATCCCCCGGATGCAACCTGACAGT
   ||  |||||| |||| | ||||||||||||||||||
   TAAGGTTGCCCCAGGAACCGCCAGGATGCAACTTGGTGAT
            610            620            630            640

--V--D-------H------------------S-------L-
    T  I  L  P  D  E  K  E  H  V  N  R  I
   CACAATCCTCCCGACGAAAAGGAACACGTTAATAGGATT
   |||||||| ||||||||||||| ||||| |||| |
   TGTCGATCTACATGACGAAAAGGAGCATGTTAGCCGTCTA
            650            660            670            680
```

*FIG. 5E*

```
  -S-----  -----N-----  ---T-----  -----T-----  -----L-----  -L---
   C   S    R   D   P   G   E   T   A   D   R   N   M
  TGTTCAAGAGATAGACCGGGTGAAACGGCAGATAGAAATA
   ||||||||||||||||||||||||||||||||||||||||
  TCTTCACGGAATAGGACCGGCGAGAAAACAGATCTACTAA
            690          700          710          720

------  -----A-----  -----S---C-----  -----L   V   D
   L   R   T   L   N   A   V   Y   A   S   L   V   D
  TGCTCAGAACACTCAATGCCCGTATACGCATCTTTGGTGGA
   ||||||||||||||||||||||||||||||||||||||||
  TGCTCAGGGCACTTAAATGCAGTGTATTCCTGTTTAGTAGA
            730          740          750          760

---  -I---M-----  -----H---I-----  -----S-----
   T   V   K   Y   A   N   L   T   C   P   Y   E   K
  CACGGTTAAATACGCAAATCTAACATGCCCTTACGAGAAA
   ||||||||||||||||||||||||||||||||||||||||
  CACTATTATGTACGCAAATCATATTTGTCCCTACAGTAAG
            770          780          790          800
```

```
          ----------R--------|                          |
 L  L  A  I  F  K  R  K  E  L  C  S  E  N
CTCCTGGCCATTTTTAAACGGAAAGAGCTGTGTAGCGAAA
   | |||||||  ||   ||||||    |||  ||||
  CTTTTAGCGATATATTTAAGCGGGAGAATTATGT
      930       940       950       960

G  E  L  L  T  Q  Y  S  W  I  L  W  G
ATGGGGAGCTGTTAACTCAGTATTCTTGGATATTGTGGGG
      970       980       990       1000

L  L  T  K  L  H  T  I  N  V  E  L  F
ATTACTGACTAAAACTACACACCATTAATGTCGAATTATTT
      1010      1020      1030      1040

|---V--E--L--L
                  C  A  S  A  I
 D  I  S  G  M  S  R  R  E
GACATTAGCGGTATGTCACGTCGAGAATGCGCCAGCGCTA
      1050      1060      1070
                               TGTGTAGAACTGC
                                  1080
```

FIG. 5H

```
-----D-------S----------V--H--S--
   M  H  T  M  P  E  R  L  S  T  L  A  S
TAATGCATACTATGCCGGAGAGATTGTCTACTCTCGCTAG
|||||||||||||||||||||||||||||||||||  |||
TTATGGATACTATGTCGGAGAGATTGGTAACACATAGTAG
       1090           1100          1110          1120

-----A--F-----I-----A---------L--A-
   W  N  D  L  C  E  L  E  D  D  V  I  S
CTGGAATGATTTATGCCGAGCTTGAAGATGATGTAATTTCC
||||||||||||||||||||||||||||||||||||
CTGGAATGATGCCTTCGAGATTGAAGCTGATGTACTAGCC
       1130          1140          1150          1160

-----E-----A--M--*|
   Y  N  K  G  M  C  N  E  V  G  A  S  R  *
TATAATAAGGGAATGTGTAACGAGGTTGGAGCGTCTCGAT
||||||||||| |||||         
TATAATAAAGAGATGGCTATGTAA
       1170          1180          1190          1200

AATTCTTCTTAATCTGCTGGTATTGGTTACTGCCATAACT
       1210          1220          1230          1240
```

FIG. 51

TATTATTGGTCCATGCTAGAATAGTCATACGCTACGATCT
     1250          1260          1270          1280

GTTGCTATATATGACTATCGCCAAACTGTTAAACCCGCGA
     1290          1300          1310          1320

AGAATATATTTCATATAAACCTAAGGGCCCCTCAGTCTGA
     1330          1340          1350          1360

TTTTTTGTGAAAACGTGTATACCA
     1370          1380

```
  1 CAGCTGCCTATGTAGTGAAATCTATACTGGATTT
    ATCATAACTAGTTTACTTGTTTGTATATTAGTAGCGCTATCT
    TGACCAAATCGTTGTTCACATCTTGGCCATATACGTATTGATC

121 GTTGTTTCGAACCGCGAATAAAAACTTTCATACATAC
    TAAACGATGGAGTTGTGTTTTATGAGCGTTGAAAACAAAGGT
    ACCATCGGTTTAAAACTAAGTTGCATATCGTAATCCACAAAA

241 ATCATTTTATACATCATCCCGAAGAGACACCAAACG
                                  M  L  T  P  R  V
    TAACCCTCTACATATCTTCCCTCATGCTCACGCCGCGTGTGT
     L  R  A  L  G  W  T  G  L  F  F  L  L  L  S
    TACGAGCTTTGGGGTGGACTGGACTCTTTTTTTTGCTTTTAT
                   P  S  N  V  L  G  A  S  L  S  R

361 CTCCGAGCAACGTCCTAGGAGCCAGCCTTAGCCGG
     D  L  E  T  P  P  F  L  S  F  D  P  S
    GATCTCGAAACACCCCATTTCTATCCTTTGATCCATCCA
```

FIG 6B

```
        N   I   S   I   N   G   A   P   L   T   E   V   P   H   A   P
        ACATTTCAATTAACGGGCGCCTTTAACTGAGGTACCTCATGCAC

S   T   E   S   V   S   T   N   S   E   S   T
        481 CTTCCACAGAAAGTGTCAACAAATTCGGAAAGTACC

N   E   H   T   I   T   E   T   G   K   N   A   Y
        AATGAACATACCATAACAGAAACGACGGGCAAGAACGCATACA

I   H   N   A   S   T   D   K   Q   N   A   N   D
        TCCACAACAATGCGTCTACGGACAAGCAAAATGCGAACG

T   H   K   T   P   N   I   L   C   D   T   E
        601 ACACTCATAAAACGCCCAATATACTCTGCGATACGGA

E   V   F   V   F   L   N   E   T   G   R   F   V   C
        AGAAGTTTTGTGTTTCCTTAACGAACGGGAAGATTTGTTTGT

T   L   K   V   D   P   P   S   D   S   E   W   S   N
        ACTCTCAAAGTCGACCCCCCTCGGATAGTGAATGGTCCA

F   V   L   D   L   I   F   N   P   I   E   Y
        721 ACTTTGTTCTAGATCTTGATCTTTAACCCAATTGAATA

H   A   N   E   K   N   V   E   A   A   R   I   A   G
        CCACGCCAACGAAAAGAATGTGGAAGCGGCGTATCGCTGGT
```

```
L   Y   G   V   P   G   S   D   Y   A   Y   P   R   Q
CTCTATGGAGTCCCCGGATCAGACTATGCATACCCACGTC

S   E   L   I   S   S   I   R   D   P
841 AATCTGAATTAATTCTTCGATTCGACGAGATCCCC

Q   G   T   F   W   T   S   P   S   P   H   G   N   K
AGGGCACATTTTGGACGAGCCCATCACCTCATGGAAACAA

Y   F   I   W   I   N   K   T   N   T   M   G   V   E
GTACTTCATATGGATAAACAAAACAACCAATACGATGGGCGTGG

I   R   N   V   D   Y   A   D   N   G   Y
961 AAATTAGAAATGTAGATTATGCTGATAATGGCTAC

M   Q   V   I   M   R   D   H   F   N   R   P   L
ATGCAAGTCATTATGCGTGACCATTTTAATCGGCCTTTAA
I   D   K   H   I   Y   I   R   V   C   Q   R   P   A   S   V
TAGATAAACATATTTACATACGTGTGTGTCAACGACCTGCATCAG

D   V   L   A   P   P   V   L   S   G   E   N
1081 TGGATGTACTGGCCCCTCCAGTCCTCAGCGGAGAAAA

Y   K   A   S   C   I   V   R   H   F   Y   P   P   G
TTACAAGGCATCTTGTATCGTTAGACACTTTTATCCCCCTGGA
```

FIG. 6C

```
      S   V   Y   V   S   W   R   Q   N   G   N   I   A   T
     TCTGTCTATGTGTATCTTGGAGACAGAATGGAAACATTGCAA
1201 CTCCTCGGAAAGATCGGATGGAAGTTTTTGGTGGTT
      P   R   K   D   R   D   G   S   F   W   F
      E   S   G   R   G   A   T   L   V   S   T   I   T   L
     CGAATCTGGTAGAGGAGCTACGTTGGTTTCTACAATAACATTG
     GGAAATTCAGGAATTGATTTCCCCCCAAAATATCTTGTC
      G   N   S   G   I   D   F   P   P   K   I   S   C   L
      V   A   W   K   Q   G   D   M   I   S   T   T
1321 TGGTTGCCTGGAAGCAGGGTGATATGATCAGCACGAC
      N   A   T   A   I   P   T   V   Y   H   H   P   R   L
     GAATGCCACAGCTATCCCGACGGTATATCATCATCCCCGTTTA
     TCCCTGGCTTTTAAAGATGGGTATGCAATATGTACTATAG
      S   L   A   F   K   D   G   Y   A   I   C   T   I   E
      C   V   P   S   E   I   T   V   R   W   L   V
1441 AATGTGTCCCCTCTGAGATTACTGTACGGTGGTTAGT
      H   D   E   A   Q   P   N   T   T   Y   N   T   V   V
     ACATGATGAAGCCAGCCTAACACAACTTATAATACTGTGGTT
```

*FIG. 6D*

```
          T  G  L  C  R  T  I  D  R  H  R  N  L  L
     ACAGGTCTCTGCCGGACCATCGATCGCCATAGAAATCTCC
               S  R  I  P  V  W  D  N  W  T  K  T
1561 TCAGCCGCATTCCAGTATGGGACAATTGGACGAAAAC
       K  Y  T  C  R  L  I  G  Y  P  F  D  E  D
     AAAATATACGTGCAGACTCATAGGCTACCCCTTCGATGAAGAT
       K  F  Q  D  S  E  Y  Y  D  A  T  P  S  A
     AAATTTCAAGATTCGGAATATTACGATGCAACTCCATCTG
               R  G  T  P  M  V  I  T  V  T  A  V
1681 CAAGAGGAACACCCCATGGTTATTACGGTTACGGCAGT
       L  G  L  A  V  I  L  G  M  G  I  M  T
     TTTGGGATTGGCTGTAATTTTAGGGATGGGGATAATCATGACT
       A  L  C  L  Y  N  S  T  R  K  N  I  R  L
     GCCCTATGTTTATACAACTCCACACGAAAAAATATTCGAT
                                    *
 1801 TATAATCTCATTGTTATGTAGTTGTGATTTATTAAAC
     ATATTTTTTATAACTCTAGTATTCTCCGAGTACTTATATATT
```

TATTGTCAGACAATAATGCAATAGTGGAGAAACGTGAGG

1921 GGAGTCTGTAAACAGAATACGTATAATCATCTATTTG

AATAAAAGATTGTGGTATAAATGAAGATAGCGCAAGTCATTC

CAAGCTCCCATTCTATTTAAACAATGTACAGTTTAAAGT

HVT HOMOLOGUES OF VZV62/ HSV-1 IE 175

```
 S  N  V  V  R  Y  M  C  G  N  T  V  L
TCGAATGTGGTGCGATACATGTGCGGGAACACGGTACTCC
         10        20        30        40

P  P  D  P  H  G  T  P  V  V  I  N  V  P
CCCCGGATCCCCATGGCACCCCCGTGGTGATCAACGTTCC
         50        60        70        80

E  G  T  S  E  T  M  A  E  L  T  V  A
CGAGGGAACGTCCGAAACTATGGCGGAGCTTACTGTTGCT
         90       100       110       120

H  V  G  R  K  S  I  G  W  P  T  S  E
CACGTTGGGCGCAAGTCTATTGGGTGGCCGACCTCCGAGT
        130       140       150       160

W  H  S  A  T  I  L  Q  K  D  N  D  S  R  L  V  I  I  R
GGCATTCCGCTACAATCCTGCAGAAAGATAATGATAGTCGGCTGGTAATTATACGCC
        170       180       190       200       210
```

FIG. 7

HVT HOMOLOGUE OF RIBONUCLEOTIDE
REDUCTASE (LARGE SUBUNIT)

```
 Q   V   T   E   V   S   E   G   F   A   P   L   F
CAAGTGACCGAGGTTAGCGAAGGATTTGCCCCTTTGTTCA
         10            20           30           40

S   N   M   F   S   K   V   T   S   A   G   E   L   L
GTAACATGTTCAGCAAGGTGACAAGTGCCGGGGAACTGCT
         50           60            70           80

R   P   N   S   Q   L   M   R   E   L   R   Q   I
TAGACCCAACAGTCAATTAAATGCGGGAGCTGAGACAAATA
         90          100           110           120

Y   P   D   N
TATCCCGATAAT
        130
```

FIG. 8

MDV HOMOLOGUE OF RIBONUCLEOTIDE
REDUCTASE (LARGE SUB-UNIT)

```
 G  I  M  E  G  S  D  V  P  T  E  K  S
GGGGATAATGGAAGGAAGTGATGTACCGACGGAAAAATCT
         10        20        30        40

H  S  G  R  E  R  N  R  S  M  G  I  G
CATTCTGGCCGAGAACGTAACAGATCGATGGGCATCGGCG
         50        60        70        80

V  Q  G  F  H  T  A  F  L  S  M  G  L  D
TGCAGGGCTTTCATACAGCTTTTCTATCTATGGGTCTTGA
         90       100       110       120

L  C  D  E  R  A  R  S  L  N  K  L  I
TTTATGCGATGAACGCGCTAGATCCCTCAACAAGCTAATT
        130       140       150       160

F  E  F  M  L  L  E  A  M  T  V  S  C
TTTGAATTCATGTTATTGGAGGCGATGACAGTTAGTTGCG
        170       180       190       200

E  F  C  E  R  G  L  P  P  F  A  D  F  S
AATTCTGCGAACGAGGCCTGCCGCCGTTTGCTGATTTCTC
        210       220       230       240
```

FIG. 9A

```
      N   S   Y   Y   A   R   G   R   L   H   F   D   G
TAACAGTTATTATGCAGGAGGACGTCTGCATTTCGATGGG
         250           260           270           280

W   A   N   V   E   L   A   A   V   E   E   W   N
TGGGCTAATGTAGAATTGGCTGCAGTGGAAGAGTGGAATA
         290           300           310           320
```

FIG. 9B

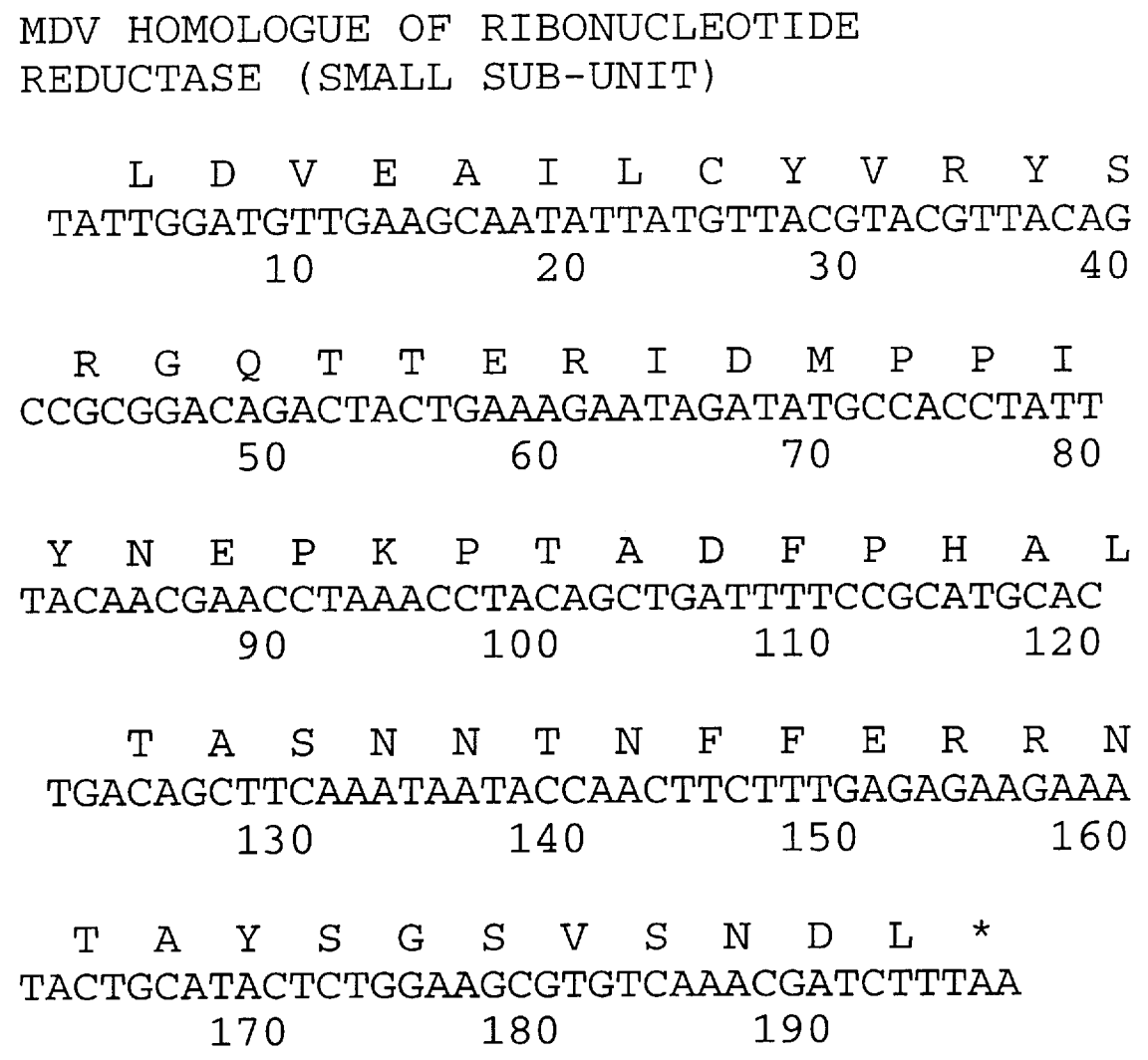

MDV HOMOLOGUE OF RIBONUCLEOTIDE
REDUCTASE (SMALL SUB-UNIT)

```
         L   D   V   E   A   I   L   C

MDV HOMOLOGUE OF HSV-1 IE-175

```
  P   I   P   V   Y   V   E   E   M   K   D

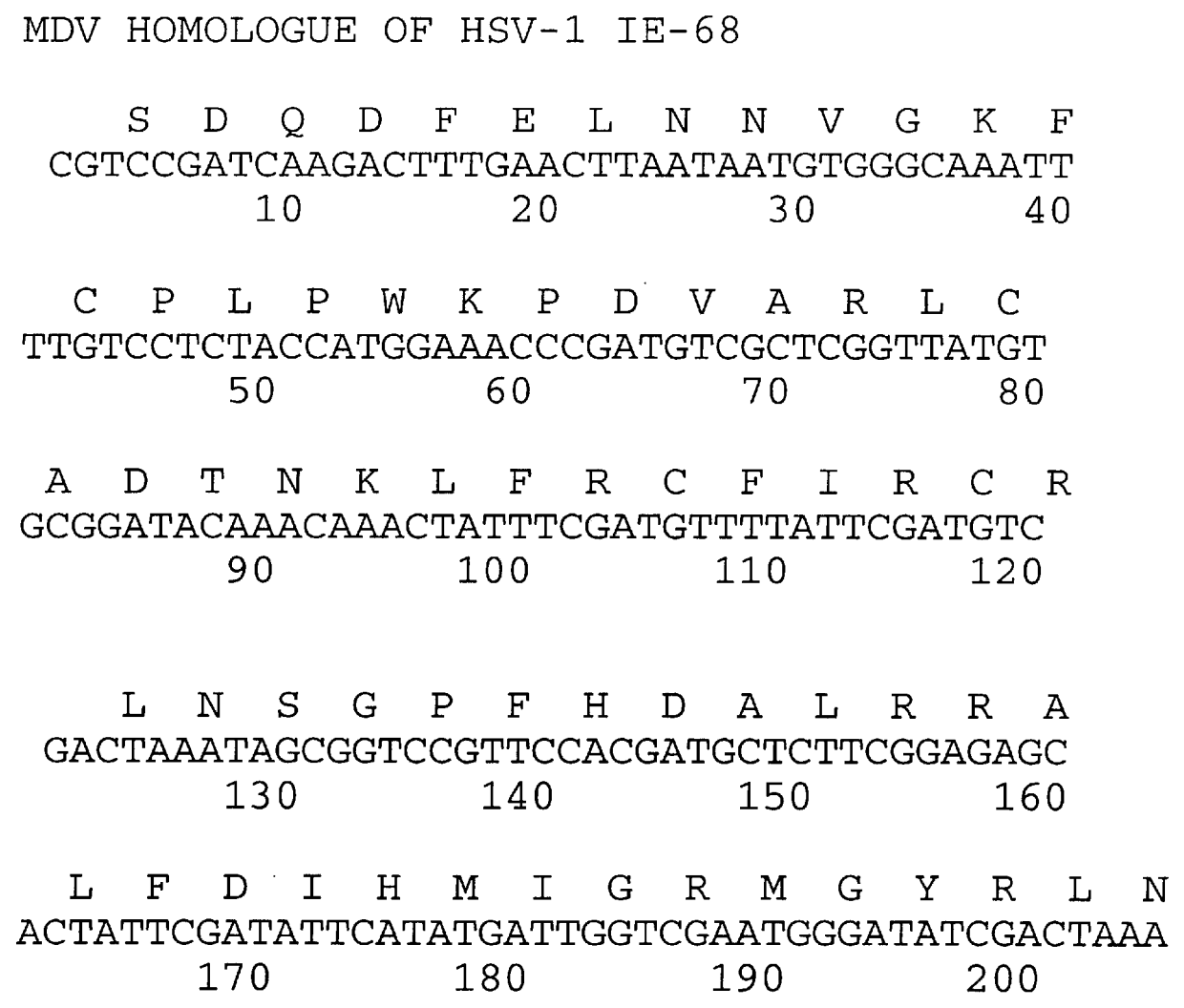

MDV HOMOLOGUE OF HSV-1 IE-68

```
            640       650       660       670       680       690       700       710       720
MDV  CGAAGTCTGCGGTCAATTTCTATTGCAATAGAGTCGGTATGACCATCCAAATTATTTAATGCTGCAGTGGCGCATTGTTTCGTGCAGTA
      R  L  R  R  D  I  E  I  A  I  S  D  T  H  G  D  L  N  N  L  A  A  T  A  A  N  N  R  A  T 730       740       750       760       770       780       790       800       810
MDV  ATGATCGCAAGTTGTCGTTCCATATTGGCCGGTTAGATGTAAAATACCGGTTCCTCCAGAACTCGATGGGCCATGGGGAGCTATAAAG
      I  I  A  L  Q  R  E  M  N  A  R  N  S  T  F  V  P  E  K  W  F  E  I  P  W  P  P  A  I  F 820       830       840       850       860       870       880       890       900
MDV  TTCTTCACATGGCAGGAACATTCCATTCCATGCCTGTCAATATTCTCGCGTCCCAAATAAAGTTGCCATGATGGTGCTACTCGAT
      N  K  V  D  A  P  F  M  E  M  G  D  G  T  L  I  R  A  D  W  I  F  N  A  M 910       920       930       940       950       960       970       980       990
MDV  ATAATCAGACAGAAGTTACAGGGAAACGCCACATGAGAAAATAATACTACAAGCTTAAACTACATTTAAACTACACAAGTTATAAAAGTTACGGTCTCTG
                                                                                            P  R  Q 1000      1010      1020      1030      1040      1050      1060      1070      1080
MDV  AACAAGACGGGCGATAATATTAGCCATGTTTCGCATAGCCGTACCTCCCGTTCCCTGATTATTTGAAAATGATAAAGTAGCCGTTTT
      V  L  R  A  I  I  N  A  M  N  R  M  A  T  G  G  T  R  E  Q  N  N  S  F  S  L  T  A  T  K 1090      1100      1110      1120      1130      1140      1150      1160      1170
MDV  ATTACAAGCTATATGATTCCTCAAATCCGTTACGTTAGCAGACGCCTTTCCACTGGTCGTTGTATATGTATCGTGTTTGTATTATGACG
      N  C  A  I  H  N  R  L  D  T  V  N  A  S  A  K  G  S  R  R  Q  I  H  I  T  N  T  N  H  R 1180      1190      1200      1210      1220      1230      1240      1250      1260
MDV  ATTACAAGCTATATGATTCCTCAAATCCGTTACGTTAGCAGACGCCTTTCCACTGGTCGTTGTATATGTATCGTGTTTGTATTATGACG
      N  C  A  I  H  N  R  L  D  T  V  N  A  S  A  K  G  S  R  R  Q  I  H  I  T  N  T  N  H  R

MDV  TTTTAAAATTTTATGAGTGTCAGTTATCCGTTGCTTTATAGTCAGACATAGTCTATGAAAATCAGTCACTAT
      K  L  I  K  H  T  D  T  I  R  A  K  Y  D  S  A  T  A  L  I  S  C  L  R  H  F  D  T  V  I 1270      1280      1290      1300      1310      1320      1330      1340      1350
```

```
          R   K   D   A   S   T   H   F   L   I   S   G   T   P   I   K   D   S   K   A   D   L   I   K   S   L   L   S   K   V
HVT   CGTAAAGACGCTAGTAGTACACACTTTCTTTATATGGGGAACGCCCATAAAAGATAGCAAAGCCGATTTAATTAAATCGTTGTCTAAAGTC
          4250        4260        4270        4280        4290        4300        4310        4320        4330

I   R   P   I   S   G   H   T   R   P   L   S   A   I   Q   H   L   F   L   L   R   S   A   Y   A   L   D   I   P   R
HVT   ATTCGACCAATTTCCGGACACATACACGTCCCTTATCTGCAATACAACATCTATTCCTTTTGAGATCCGCTTATGCATTGGATATACCCCGT
          4340        4350        4360        4370        4380        4390        4400        4410        4420

Q   N   G   S   L   S   E   Q   V   S   T   V   A   L   S   F   I   E   N   I   H   S   E   A   M   R   D   I   L   S
HVT   CAAAACGGATCTTTGAGCGAACAGGTATCTACAGTGGCACTGGCCATGAGGACATTCTGTCA
          4430        4440        4450        4460        4470        4480        4490        4500        4510

W   N   T   T   K   H   A   L   Y   Y   A   F   A   S   I   L   Q   R   P   L   T   E   W   G   A   S   R   N   A
HVT   TGGAACACTACAAAGCACGCGTTGTATTATGCATTCGCGAGTATTTTGCAACGGCCACTGACCGAATGGGGCGCCTCAAGAAATGCA
          4520        4530        4540        4550        4560        4570        4580        4590        4600

R   R   A   I   L   L   A   S   S   M   C   T   E   E   H   V   I   A   T   E   L   A   I   Q   E   L   Y   V   K   I
HVT   CGGAGGGCAATATTGCTAGCATCATCGATGTGTACAGAAGAGCATGTTATCGCAACTGAGTTGGCTATTCAAGAACTGTATGTCAAAATC
          4610        4620        4630        4640        4650        4660        4670        4680        4690

R   S   N   A   D   P   I   H   L   L   D   V   Y   T   P   C   L   S   S   L   R   L   D   L   S   E   H   H   R   I
HVT   AGAAGTAATGCCGACCCAATACACCTTCTAGACGTATATACACCATGTCTTTCTTCACTACGATTGGACCTTTCCGAACACCATCGGATA
          4700        4710        4720        4730        4740        4750        4760        4770        4780

Y   A   M   A   D   V   V   F   Y   P   D   I   Q   Q   Y   L   K   K   K   S   H   E   G   N   M   K   E   D   D   L
HVT   TACGCAATGGCAGATGTAGTTTTCTATCCAGACATTCAGCAGTATTTGAAAAAAAAATCCCATGAGGTAATATGAAGGAAGATGATGATCTC
          4790        4800        4810        4820        4830        4840        4850        4860        4870
```

*FIG. 14E-1*

```
        E  T  K  A  E  Y  I  L  T  K  L  R  S  P  L  I  R  T  L  S  A  Y  A  S  E  V  L  S  C  S
HVT  GAAACAAAGGCCGGAATACATCCTCACCAAGCTTAGGTCGCCGTTGATCAGAAGCTTGCCTATGCTGTCTGCTTATGCAAGTATTGTCCTGCTCC
            4880          4890          4900          4910          4920          4930          4940          4950          4960

D  Q  D  L  L  E  I  N  A  I  L  I  L  P  V  S  G  I  G  S  Y  V  V  S  R  R  A  G  M  Q
HVT  GACCAGGATCTATTAGAAATAAATGCTATTTTAATTCTGCCCGTTTCTGGGAGCTATGTGGTAGTCTCTGAAGGGCAGGAATGCAA
            4970          4980          4990          5000          5010          5020          5030          5040          5050

G  I  V  Y  T  V  D  G  V  D  V  N  N  Q  L  F  I  T  Y  T  R  M  P  C  T  T  T  I  G  N
HVT  GGCATTGTTTATACCGTAGACGGTGTTGATGTTAACAATCAGCTTTTTATAACATATACCAGGATGCCCGTGCACTACAACGATAGGTAAC
            5060          5070          5080          5090          5100          5110          5120          5130          5140

I  V  P  T  V  L  S  R  P  S  G  K  T  C  P  Y  C  G  C  V  L  R  Y  S  A  D  G  N  I
HVT  ATTGTTCCAACAGTATTGTCAAGACCCTCGGGAAAAACGTGTCCGTATTGCGGCTGTGTTTTGGTGCGATATTCCGCCGATGGAAATATC
            5150          5160          5170          5180          5190          5200          5210          5220          5230

R  Y  S  I  Y  I  S  S
HVT  CGCTATTCTATTTACATTTCGTCCC
            5240          5250
```

FIG. 14F

```
G  R  R  K  Y  D  A  L  V  A  -  F  V  L  G  R  A  C  G  R  P  I  Y  L  R  E
GGGACGACGCAAATATGATGCTCTAGTAGCAT4GTTTGTCTTGGGCAGAGCATGTGGGAGAGACCAATTTATTTACGTGAA

Y  A  N  C  S  T  N  E  P  F  G  T  C  K  L  K  S  L  G  W  D  R  R  Y  A
TATGCCAACTGCTCTACTAATGAACCATTTGGAACTTGTAAATTAAAGTCCCTAGGATGGTGGGATAGAAGATATGCAA

M  T  S  Y  I  D  R  D  E  L  K  L  I  I  A  A  P  S  R  E  L  S  G  L  Y  T  R
TGACGAGTTATATCGAGATGAATTGAAATTGATTATTGCAGCACCCAGTCGTGAGCTAAGTGGATTATATACGCG

L  I  I  N  G  E  P  I  S  S  D  I  L  L  T  V  K
TTTAATAATTATTAATGGAGAACCCATTTCGAGTGACATATTACTGACTGTTAAA
```

FIG. 15

VIRAL VACCINES

This is a division of application Ser. No. 08/081,932 filed Jun. 23, 1993, now U.S. Pat. No. 5,558,860, which is a continuation in part of application Ser. No. 07/669,392 filed Apr. 29, 1991 (now abandoned).

BACKGROUND OF THE INVENTION

1. Field of the Invention

The present invention relates to viral vaccines which may be used to provide immunity against disease and to nucleotide sequences for inclusion in such vaccines.

2. Description of Related Art

Herpesviruses are large double stranded DNA viruses consisting of an icosahedral capsid surrounded by an envelope. The group has been classified as alpha, beta and gammaherpesviruses on the basis of genome structure and biological properties [Roizman, B. et al. (1981) Intervirology 16, 201–217]. Avian herpes viruses include Marek's Disease Virus (MDV) (a gammaherpesvirus) which causes a lymphomatous disease of considerable economic importance in chickens [reviewed in Payne, L. N. (ed) Marek's Disease (1985), Martinus Nijhoff Publishing, Boston] and Infectious Laryngotracheitis Virus (ILTV) (an alphaherpesvirus) which causes an acute upper respiratory tract infection in chickens resulting in mortality and loss of egg production.

A recent unexpected finding in our laboratory is that there is sufficient amino acid homology between MDV, ILTV and mammalian herpesviruses, particularly varicella zoster (VZV) and Herpes Simplex Virus (HSV) to allow identification of numerous conserved genes. These include the MDV and Herpesvirus of Turkeys (HVT) homologues of glycoproteins gB, gC and gH of HSV: the ILTV, MDV and HVT homologues of TK and ribonucleotide reductase genes and the ILTV homologue of gB and genes 34 and 35 of VZV [Buckmaster, A. et al (1988) J. gen. Virol, 69, 2033–2042].

Strains of MDV have been classified into three serotypes. Type 1 comprises pathogenic strains and their attenuated derivatives. Type 2 are a group of naturally-occurring non-pathogenic strains and type 3 is HVT. For more than a decade, vaccination with HVT has been remarkably effective in controlling Marek's disease. However, in recent years, new strains of MDV have been isolated which cause disease despite vaccination with HVT. Losses due to these 'very virulent' strains have occurred in parts of the U.S.A., Europe and the Middle East. Although the degree of protection can be improved by using a mixture of HVT, type 2 MDV and attenuated derivatives of very virulent strains for vaccination, the results have been erratic. These observations and the fact that there are MDV type-specific epitopes that are not shared by HVT or type 2 MDV have led us to the conclusion that improved vaccines might be constructed which are antigenically more related to MDV than existing vaccines. [Reviewed by Ross and Biggs in Goldman J. M. and Epstein M. A. (eds) Leukaemia and Lymphoma Research, Vaccine Intervention against Virus-Induced Tumour, p 13–31, Macmillan, 1986].

A number of herpesvirus antigens have been shown to confer protective immunity when expressed in a recombinant vaccinia virus. These include the gB gene of HSV [Cantin E. M. et al (1987) Proc. Natl. Acad. Sci. U.S.A. 84, 5908–5912], gD of HSV [Paoletti, E. et al (1984) Proc. Natl. Acad. Sci. U.S.A. 81, 193–197] and gp50 of pseudorabies virus (PRV), a homologue of HSV gD [Marchioli, C. C. et al (1987) J. Virol. 61, 3977–3981]. Because of the absolute requirement of gB for virus penetration and infectivity and because it is conserved among herpesviruses, gB and its homologues are important immunogens. Moreover, the presence of gB at the surface of infected cells has been shown to be an important target for humoral and cell-mediated immune responses [Blacklaws, B. A. et al J. gen. Virol. 68, 1103–1114 (1987); McLaughin-Taylor, E. et al (1988) J. gen. Virol. 69, 1731–1734]. The recently described glycoprotein gH of HSV is also essential for infectivity and may also be an important immunogen [Desai, P. J. et al (1988) J. gen. Virol. 69, 1147–1156]. It has also been shown that gIII of pseudorabies virus (PRV), a homologue of gC, is a major target for neutralizing antibody and for cytotoxic T cells although it is a non-essential protein. Also of interest is the unexpected participation of immediate early proteins in T cell mediated cytotoxic reactions in cells infected with cytomegalovirus (CMV) [Kozinowski U. H. et al (1987) J. Virol. 61, 2054–2058]. Similar antigens could play an important role in the rejection of latently infected and transformed lymphocytes in Marek's disease since immediate early RNA transcripts have been detected in lymphoblastoid cell lines established from Marek's disease tumours.

Although many recombinant vaccines have been constructed using the poxvirus vaccinia as a vector, there are also reports of the use of herpesviruses as vectors for the expression of foreign genes. Thus hepatitis antigen has been expressed in HSV [Shih, M. F. et al (1984) Proc. Natl. Acad. Sci. U.S.A. 81, 5867–5870] and human tissue plasminogen activator has been expressed in PRV [Thomsen, D. R. et al (1987) Gene 57, 261–265. In both cases, foreign genes were inserted in cloned fragments of non-essential herpes genes which were then introduced into the virus vector by homologous recombination. The hepatitis virus gene was fused to a herpesvirus promoter and the recombinant DNA was inserted within the TK gene of HSV. Homologous recombination following co-transfection of the recombinant DNA and wild-type HSV DNA resulted in TX– virus clones that expressed the hepatitis antigen.

In the case of PRV, the gX gene mapping in $U_s$ was used as the site for insertion of the foreign gene. The strategy used involved insertion of the TK gene of HSV in the gX gene of a PRV mutant that had a defect in its TK gene resulting in a TK positive virus. The human tissue plasminogen activator gene was then inserted within a cloned fragment of HSV TK and the recombinant was introduced into the PRV mutant by homologous recombination. TK– virus was selected which expressed the human gene (Thomsen et al as above). Similarly, VZV has been used as a vector [Lowe et al (1987) Proc. Natl. Acad. Sci. U.S.A. 84, 3896–3900]. Several herpesvirus genes have also been shown to be associated with virulence and to be non-essential for growth in vitro. These include the TX genes of HSV [Jamieson, A. T. et al (1974) J. gen. Virol. 24, 465–480; Field, H. and Wildy, P., (1987) J. Hygiene (Cambridge) 81, 267–277] and of PRV. Indeed it has long been known that PRV is readily attenuated by deletion of TK activity [Tatarov, G. (1968) Zentralbl. Vet. Med 15B, 848–853]. Furthermore, attenuation of the Bartha strain of PRV has been attributed to a defect in gI, a non-essential structural glycoprotein mapping in $U_s$ [Mettenleiter, T. et al (1987) J. Virol. 61, 4030–4032].

Genes of HSV mapping in the internal repeat region (TRS) flanking the long unique sequence have also been associated with pathogenicity (Rosen, A. et al (1986) Virus Research 5, 157–175; Thompson, R. L. et al (1983) Virology 131, 180–192]. Several additional genes of HSV have been shown to be non-essential for growth in vitro although it is not known whether they are associated with virulence. These include UL24 [Sanders, P. G., (1982), J. gen. Virol. 63, 277–295], large subunit of ribonucleotide reductase [Goldstein D. J. and Weller, S. K. (1988) J. Virol. 62, 196–205], gC [Draper K. G. et al (1984) J. Virol. 51, 578–585], dUTPase [Fisher, F. B. & Preston, V. G. (1986,) Virology 148, 190–197], and $U_L$ 55 and $U_L$ 56 [MacLean, A. R. & Brown, S. M. (1987) J. gen. Virol. 68, 1339–1350]. Moreover there is evidence that several genes of HSV mapping in $U_s$ are also non-essential for growth in vitro [Weber, P. C. et al (1987) Science 236, 576–579].

WO 88/07088 (published only on 22 Sep. 1988) disclosed hybrid viral vectors based on HVT or MDV and including a gene of interest in a non-essential site, such as the TK region or the region encoding protein A. Protein A, in this context, appears to be the same as gC, disclosed by Velicer and Coussens [Coussens, P. M. & Velicer, L. F. (1988) J. Virol. 62, 2373–2379].

SUMMARY OF THE INVENTION

One aspect of the present invention provides a nucleotide sequence substantially free of the sequences which would adjoin it in the wild-type virus associated with the sequence, the sequence being selected from the group consisting of:

(a) the MDV homologue of the HSV gB gene, (b) the MDV homologue of the HSV gH gene, (c) the TK gene of MDV, (d) the MDV homologue of the immediate early gene IE-175 of HSV-I, (e) the MDV homologue of the immediate early gene IE-68 of HSV-I, (f) the MDV homologue of the HSV gD gene, and minor variations thereof.

In addition, the TK sequence of HVT, referred to hereinafter sometimes as sequence (x), and the MDV analogue of HSV gC, referred to hereinafter sometimes as sequence (y), and minor variations of either may be used as insertion sites for certain heterologous sequences or as deletion sites to obtain less virulent viruses but are not novel per se.

Each of sequences (a) to (f), (x) and (y) may be associated with further elements such as suitable stop and start signals and other 5' and 3' non-coding sequences, including promoters, enabling expression of the sequence. Such further elements may be those associated with the sequence in its naturally-occurring state or may be heterologous to that sequence.

In particular the promoter may be one associated with one of the sequences (d) and (f) above.

The term "minor variations thereof" is intended to include changes in the nucleotide sequences which do not affect the essential nature of the nucleotide sequences or the proteins encoded by them, for example, minor substitutions of nucleotides for one another. In the case of sequences which are intended for insertion into a vector to encode an antigen, the "essential nature" of the sequence refers to the protein or glycoprotein encoded. Conservative changes in the nucleotide sequences which give rise to the same antigen will clearly be included, as will changes which cause conservative alterations in the amino acid sequences which do not affect adversely the antigenic nature of the antigen. In particular, antigenic portions of the antigen sequences may be used alone, for example, the regions corresponding to nucleotides 816–863, 1377–1595, 1377–1630 or 1824–1985 of MDV gB, or nucleotides 483–633, 843–933 or 1203–1278 of MDV gC, and minor variations thereof. These sequences and the peptides encoded thereby form further aspects of the invention. In the case of a sequence which is an insertion site, it is necessary only that the sequence should be non-essential for the infectivity and replication of the virus and have sufficient homology with the defined sequence to enable recombination to occur. Thus an insertion of the nucleotide into the sequence could completely change the reading frame from then on in a downstream direction. In the case of an antigen-encoding sequence this would usually alter the amino acid sequence undesirably (depending on where the frameshift occurred), but in the case of an insertion site, the degree of homology would be almost the same, thereby allowing recombination to take place with almost the same ease.

Generally speaking, in an insertion site, if a nucleotide homology of at least 75% is present, the sequence is regarded as a "minor variation". Preferably, the sequence is at least 80, 85, 90, 95 or 99% homologous. It will be appreciated that such degrees of homology relate to substantially the entire portion of each sequence (a) to (f) and (x) defined above. Shorter sequences may be used as probes in the identification or isolation of such longer sequences, but in this case the degree of homology will in general need to be greater in order to ensure accurate hybridization.

Thus, a further aspect of the invention provides sub-sequences of at least 13 nucleotides having at least 90% (preferably 95%, 99% or 100%) homology to at least one portion of any of the said sequences (a) to (f), (x) and (y) above.

In the above list, sequences (a), (b), and (d) to (f) are useful as antigen-expressing sequences and sequence (y) is useful as an insertion site for heterologous sequences. Sequence (c) is useful for deletion to provide TK– mutants.

The sequences may readily be isolated from naturally-occurring HVT and MDV viruses, using the sequence information given herein and standard techniques, for example involving the preparation of oligonucleotide probes and use thereof to hybridize to the naturally-occurring DNA.

The isolated polypeptides encoded by sequences (a), (b) and (f) above are novel and form a further aspect of the invention, together with minor variations thereof, and any glycosylated forms thereof which result from expression of the said sequences in MDV-susceptible cells.

A second aspect of the invention provides MDV mutants which are insertional or deletional mutants in the TK gene.

The mutation may be in the coding or non-coding sequences of the region identified.

An MDV antigen-expressing gene may be isolated from a virulent strain of MDV and inserted into the TK region of a less virulent strain of MDV; this insertion would result in a novel "virus" if it did not result in a naturally-occurring virus.

Other heterologous antigen-encoding sequences may be included, as well as an MDV antigen-encoding sequence, for example.

The heterologous sequence may alternatively be one coding for an antigen associated with any one of the following diseases: avian encephalomyelitis (epidemic tremor), avian influenza (fowl plague), avian leukosis, avian paramyxoviruses other than Newcastle disease (PMV2 to PMV7), avian reovirus diseases (enteric disease, tenosynovitis), chicken anaemia (caused by chicken anaemia agent), coccidiosis, egg drop syndrome (EDS76), fowl pox, infectious bronchitis, infectious bursai disease (Gumboro), inclusion body hepatitis (adenovirus), lymphoproliferative disease of turkeys, Newcastle disease, reticuloendotheliosis in chickens, reticuloendotheliosis in turkeys, rotavirus enteritis, turkey haemorrhagic enteritis, and turkey rhinotracheitis. The sequence may alternatively encode paramyosin (a muscle protein common to all invertebrate parasites) or an antiscenic part thereof, somatostatin or a growth-promoting part thereof, or an immune regulator.

The vectors in accordance with the invention will then provide multivalent vaccine protection.

The mutant viruses are potentially useful in vaccines as attenuated viruses, without necessarily having a heterologous sequence inserted.

A convenient process for preparing the deletional or insertional mutants of the second aspect of the invention comprises simply introducing into a suitable cell, for example, by co-transfection, a deletional or insertional mutant version of the TK region and either whole viral DNA or a whole virus (for example, the wild-type virus). The naked DNA of such viruses has been found to be infectious, provided that it has not been sheared. A calcium phosphate precipitate of the DNA is generally advantageous. Suitable cells include chicken embryo fibroblasts, chicken kidney cells, and duck embryo fibroblasts, all preferably grown in sub-confluent monolayers in Petri dishes. The transfected DNA and the whole viral DNA will then recombine with one another in the infected cells by homologous recombination and the desired recombinants can be screened for, for example, by the detection of hybridization to suitable probes or by an immunoassay using suitable antibodies to the gene product of the region in question.

For homologous recombination to take place, the viral DNA must replicate. At present, no cell-free replication system for MDV is known. However, if such a system becomes available, then the process of the invention could be operated therein. The environment in which the replication and recombination occur is not critical.

Regions (a), (b) and (d) to (f), which were identified above as being responsible for encoding immunologically useful viral antigens, can be inserted into suitable vectors, for example into HVT or other vectors such as fowlpox-virus, bacteria, or fungi. In the case of viral vectors, especially herpesvirus vectors and poxvirus vectors, such insertion can be achieved by recombination between the antigen-encoding sequence, flanked by suitable non-essential sequences, and the vector's genome in a suitable host cell as described above. When HVT is the vector, the promoter will usually be an HVT or MDV vector. When fowlpox-virus or other virus is the vector, the promoter will usually be a promoter which is endogenous to the vector. In the case of bacteria and fungi, the antigen-encoding sequence may be inserted using known or yet-to-be-discovered techniques of DNA manipulation. A non-pathogenic strain of Salmonella may be used as such a host. The heterologous sequence may be inserted into the host's genome or be carried on an independently replicating plasmid. A promoter which is endogenous to the host will usually be used to control expression of the heterologous (viral antigen-encoding) sequence.

The flanking sequences which are used may comprise all, virtually all, or less of the region into which the heterologous sequence is to be inserted. If all the region is employed, then the sequence of that region will clearly still be present in the resulting virus, but the function of that region will have been deleted. If less than the whole region is used as flanking sequences, then the result will be a structural as well as functional deletion. Either approach may be used.

Thus, three strategies can be envisaged for the construction of improved Marek's disease vaccines: (1) Construction of recombinant HVT that express selected MDV genes; (2) Construction of deletional or insertional mutants of highly virulent strains of MDV, which are attenuated and hence suitable for use in vaccines; (3) Construction of recombinant viruses that express MDV proteins in other vectors such as fowlpox virus.

To prepare a vaccine in which HVT or MDV is the virus or vector, the virus is grown in suitable cells such as chick embryo fibroblasts in a standard culture medium such as 199 medium (Wellcome or Flow Laboratories) for 3 to 4 days at about 37° C. The cells are harvested by trypsinization and suspended in medium containing 10% dimethyl sulphoxide and 4% calf serum before storage in liquid nitrogen in sealed ampoules.

For vaccination, typically, day-old chicks are injected intramuscularly with about 1,000 plaque-forming units. Immunity follows within a few days.

It should be noted that MDV and HVT are cell-associated viruses and are infectious only when present in cells. Thus, a vaccine based on such viruses will always include suitable infected cells.

The vaccines of the invention may be used to protect any fowl susceptible to MDV, including commercially-reared poultry such as chickens, turkeys, ducks, and quail.

BRIEF DESCRIPTION OF THE DRAWINGS

FIG. 1 is a map of the MDV genome showing in part the BamHl site distribution and the location of the gB and TK genes.

FIGS. 2A–2R show the nucleotide sequence of the gB gene of the RB1B strain of MDV, with the numbering referring to the MDV nucleotides, the sequence of part of the HVT gB gene shown below the line, homologies indicated by vertical bars, and amino acid differences between MDV gB and HVT gB shown above the line.

FIG. 3 is a map of the HVT genome showing the positions of the gH (hatched), TK (solid black), and major capsid protein (MCP, dotted) genes, with HindIII sites shown as "H".

FIGS. 4A–4H show the nucleotide sequence of most of the HVT gH gene, with the corresponding amino acid sequence shown above the line.

FIGS. 5A–5J show the nucleotide sequence of the HVT TK gene, with the numbering referring to the HVT nucleotides, the sequence of part of the MDV TK gene shown below the line, homologies indicated by vertical bars, and amino acid differences between MDV TK and HVT TK shown above the line.

FIGS. 6A–6F show the nucleotide sequence of the gC gene of the RB1B strain of MDV, with corresponding amino acids shown above the line. The 3' terminal part of this nucleotide sequence encodes an anchoring sequence of the gC glycoprotein encoded by this gene.

FIG. 7 shows part of the nucleotide sequence of the HVT homologue of the VZV62/HSV-1 IE 175 gene, with corresponding amino acids shown above the line.

FIG. 8 shows part of the nucleotide sequence of the HVT ribonucleotide reductase (large subunit) gene with corresponding amino acids shown above the line.

FIGS. 9A and 9B show part of the nucleotide sequence of the MDV ribonucleotide reductase (large subunit) gene, with corresponding amino acids shown above the line.

FIG. 10 shows part of the nucleotide sequence of the MDV ribonucleotide reductase (small subunit) gene, with corresponding amino acids shown above the line.

FIG. 11 shows part of the nucleotide sequence of the MDV homologue of the HSV-1 IE-175 gene, with corresponding amino acids shown above the line.

FIG. 12 shows part of the MDV homologue of the HSV-1 IE-68 gene, with corresponding amino acids shown above the line.

FIG. 13 is a schematic representation of homologous recombination at a non-essential region of a viral genome and a homologous region of DNA cloned within a plasmid vector.

FIGS. 14A–14F supplement FIGS. 4 and 5 and show the nucleotide and predicted amino acid sequences from the region containing the MDV and HVT TK and gH and flanking genes. The bracketed MDV amino acid sequences are those potentially encoded by this region of nucleotide sequence if the upstream ATG triplet were the true gene initiation site. Asterisks denote stop codons. Spaces have been inserted into the sequences in order to optimize alignments. Colons between the MDV and HVT DNA sequences indicate nucleotides conserved between the two viruses. MDV amino acids are only shown in positions where they differ from that in HVT.

FIG. 15 shows the partial nucleotide sequence of the MDV homologue of HSV gD, the predicted amino acids being shown above the MDV nucleotide sequence.

DESCRIPTION OF THE PREFERRED EMBODIMENTS

Figure 1:
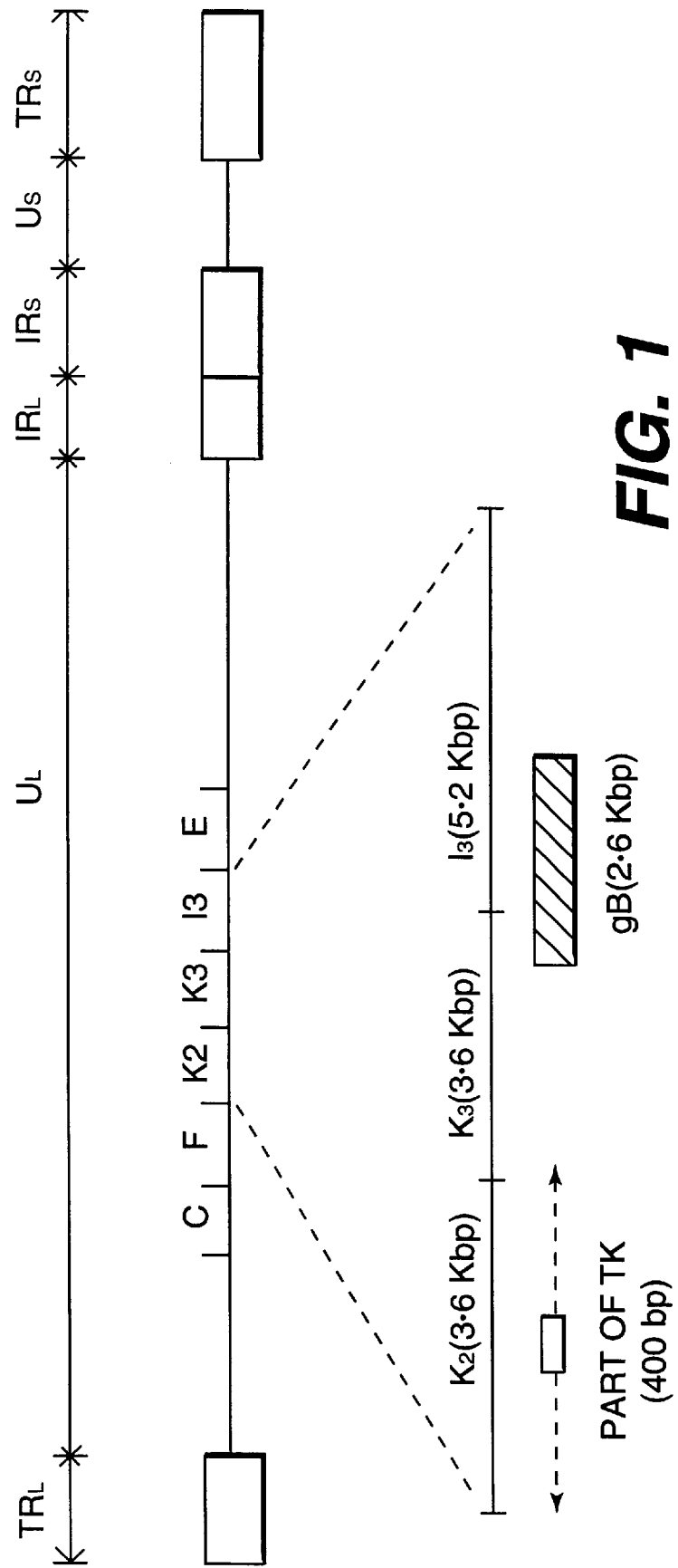

Selected short sequences of the avian herpesviruses cloned in the bacteriophage vector M13 were used as probes to identify longer fragments that might contain the entire genes of interest. This was achieved by Southern blot hybridization of restriction fragments. Full details are given below.

Virus Strains. The 'highly oncogenic' strain RB1B of MDV [Schat, K. A. et al (1982) Avian Pathol. II, 593–605] was obtained from Professor B. Calnek, Cornell University, Ithaca, N.Y., U.S.A. The virus received has been plaque purified in chicken kidney cells in tissue culture. It was passaged twice in SPF RIR chickens and 4 times in chick embryo fibroblasts (CEF). Its 'highly oncogenic' nature was demonstrated by a high incidence of gross tumours when inoculated in genetically resistant N-line chickens.

The FC126 strain of HVT [Witter, R. L. et al (1970) Am. J. Vet. Res. 31, 525–538], obtained from the Wellcome Research Laboratories, Beckenham, Kent, had been passaged 14 times in CEF. It was subsequently grown in duck embryo fibroblasts (DEF) and CEF in our laboratory. It was then plaque-purified and grown further in CEF. Viral DNA used for cloning in the present work was extracted from virus that had been passed 29 times since the original isolation.

Tissue culture. CEF were grown in roller bottles in 199 medium (Wellcome), supplemented with penicillin, streptomycin, Fungizones®, and calf serum as described previously [Ross, L. J. N. et al (1975) J. gen. Virol. 28, 37–47].

CKC were grown in 10 cm Petri dishes [Churchill, A. E. and Biggs P. M., (1967) Nature, 215, 528–530].

Isolation of IDV DNA. Cell associated RB1B was inoculated onto confluent monolayers of CEF in roller bottles at a multiplicity of infection of approximately 0.001 plaque-forming units (pfu) per cell, and the cultures were incubated at 37° C. After 3 days, the medium was discarded and replaced with fresh 199 medium containing 2% calf serum. Cells were harvested for virus purification after 2 to 3 days when cytopathic effect was extensive. Virus was obtained by rate zonal centrifugation of the cytoplasmic fraction of infected cells [Lee, Y. S. et al (1980) J. gen. Virol. 51, 245–253]. Viral DNA was extracted by treating purified virus with sarcosyl, proteinase K and Tris buffer PH 9 overnight at 37° C. and purified by rate zonal centrifugation in glycerol gradients as described previously (Lee et al, 1980). High molecular weight viral DNA was precipitated with ethanol and resuspended in 10 mM Tris pH 7.5 and ImM EDTA (TE).

Cloning of MDV DNA. One $\mu$g of MDV DNA was cut with the restriction enzyme BamHl and ligated to BamHl-cut, dephosphorylated pUC13 DNA (Pharmacia). Competent *E-coli* strain TGI cells were transformed according to standard procedures [Hanahan, D. (1983) J. Mol. Biol. 166, 557–580] and were grown in the presence of ampicillin and X-gal. White colonies were picked and tested for the presence or MDV inserts by hybridization to nick-translated MDV DNA [Grunstein M. and Hogness, D. S. (1975) Proc. Natl. Acad. Sci. U.S.A. 72, 3961]. Positive colonies were cultured in small volume and plasmid DNA isolated by the procedure of Holmes, D. S. and Quigley, M. [(1981) Anal. Biochem. 114, 193–297]. The size of the inserts was determined by electrophoresis of BamHl digests of the recombinant DNA in agarose gels. Plasmids containing MDV inserts ranging from less than 1 to 18 Kbp were obtained.

Random sequencing of viral DNA. Sonicated fragments of viral DNA were cloned into SmaI-cut, dephosphorylated M13.mplO (Amersham International PLC) and plaques containing MDV inserts were identified by hybridization to MDV DNA. The sequence was determined by the dideoxy method [Sanger, F. et al (1977) Proc. Natl. Acad. Sci. U.S.A. 74, 5463–5467] using $^{35}$S dATP.

The same procedure was used to sequence cloned fragments of MDV DNA except that plaques were identified by hybridization to labelled insert so as to avoid colonies containing pUC13 fragments.

The present invention will be better understood by reference to the following examples, which are merely illustrative of the invention and are not intended to limit the scope of the invention, which is defined in the claims appended hereto.

EXAMPLE 1 gB gene of MDV

An M13 clone of HVT homologous to the gB gene of VZV and HSV hybridized to BamHl fragment I3 of MDV (see FIG. 1). Sequencing of this fragment obtained from a BamHl library of the RB1B strain of MDV showed that two thirds of the gene, starting with the $NH_2$ terminus, was contained within I3. The remainder of the gene was identified in the adjacent restriction fragment K3. FIG. 1 shows the map position of the gene which is 2.6 Kbp long. Its mRNA has been estimated to be approximately 2.8 Kb. The translated protein is 865 amino acids long (FIG. 2). This includes approximately 20 amino acids which may be part of a signal sequence domain. The primary translated sequence of MDV gB has a few features in common with gB of other herpes viruses, such as the alignment of cysteine residues and the presence of hydrophobic sequences which are presumably capable of spanning a lipid bilayer [Pellet, P. E. et al (1985), J. Virol. 53, 243–253]. However, MDV gB has only 48% amino acid similarity with gB of HSV and has many unique features such as the insertion of 23 amino acids (residues 1851–1920, FIG. 2) and the presence of extra sites with glycosylation potential. Comparison of the sequence of MDV gB with limited sequence data (702 bases) available for HVT gB (FIG. 2) has shown 76.9% nucleic acid similarity and 87.1% amino acid similarity between these two glycoproteins. Amino acid substitutions in HVT gB compared to MDV gB were particularly marked in a region (residues 1323–1433) equivalent to a domain of HSV gB associated with virus neutralization [Pellet P. E. et al (1985) as above]. Amino acid substitutions between MDV and HVT gB were also noted in other regions of unknown function.

EXAMPLE 2
gH gene of HVT and gH gene of MDV

Figure 3:
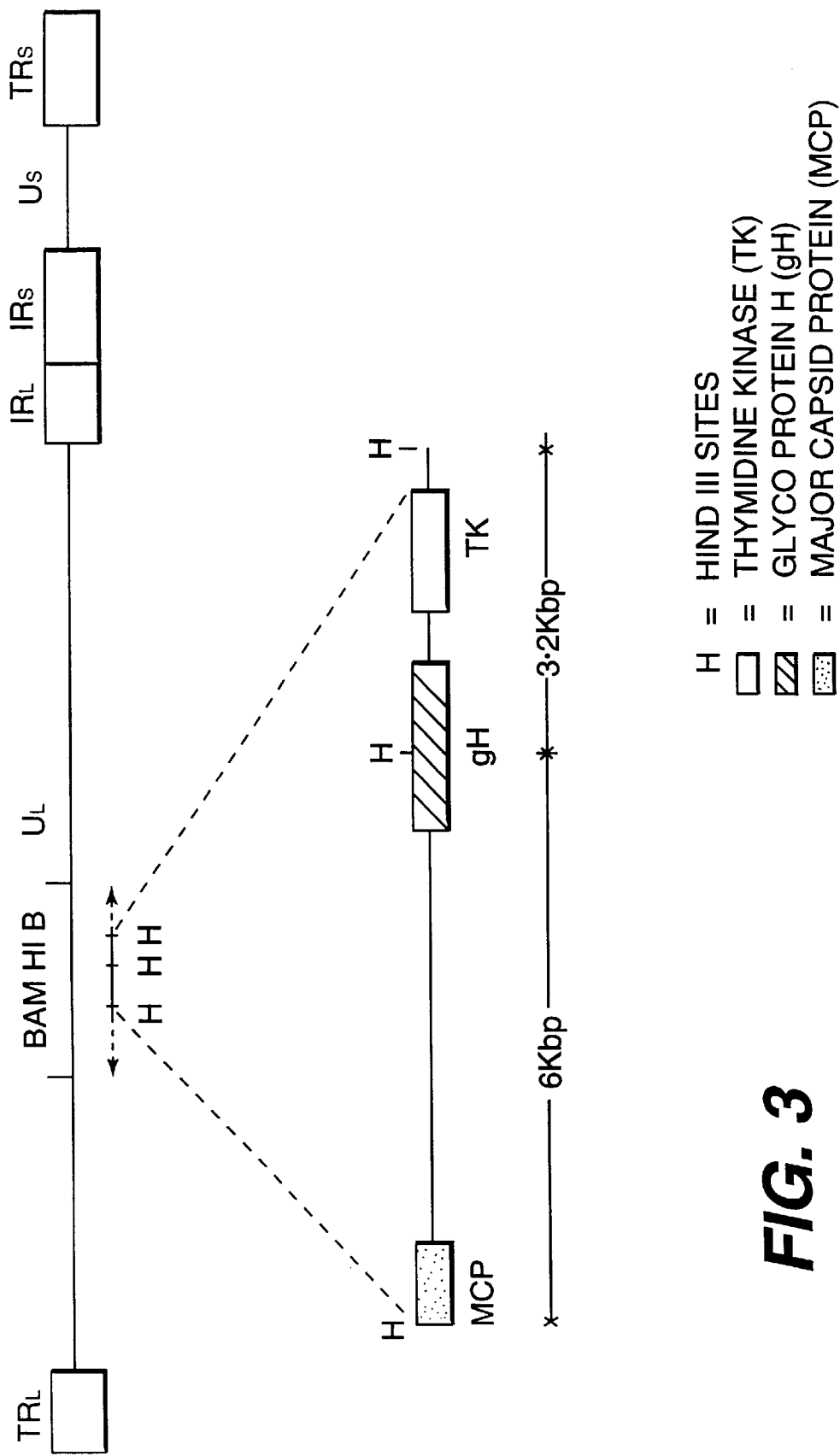
Figure 13:
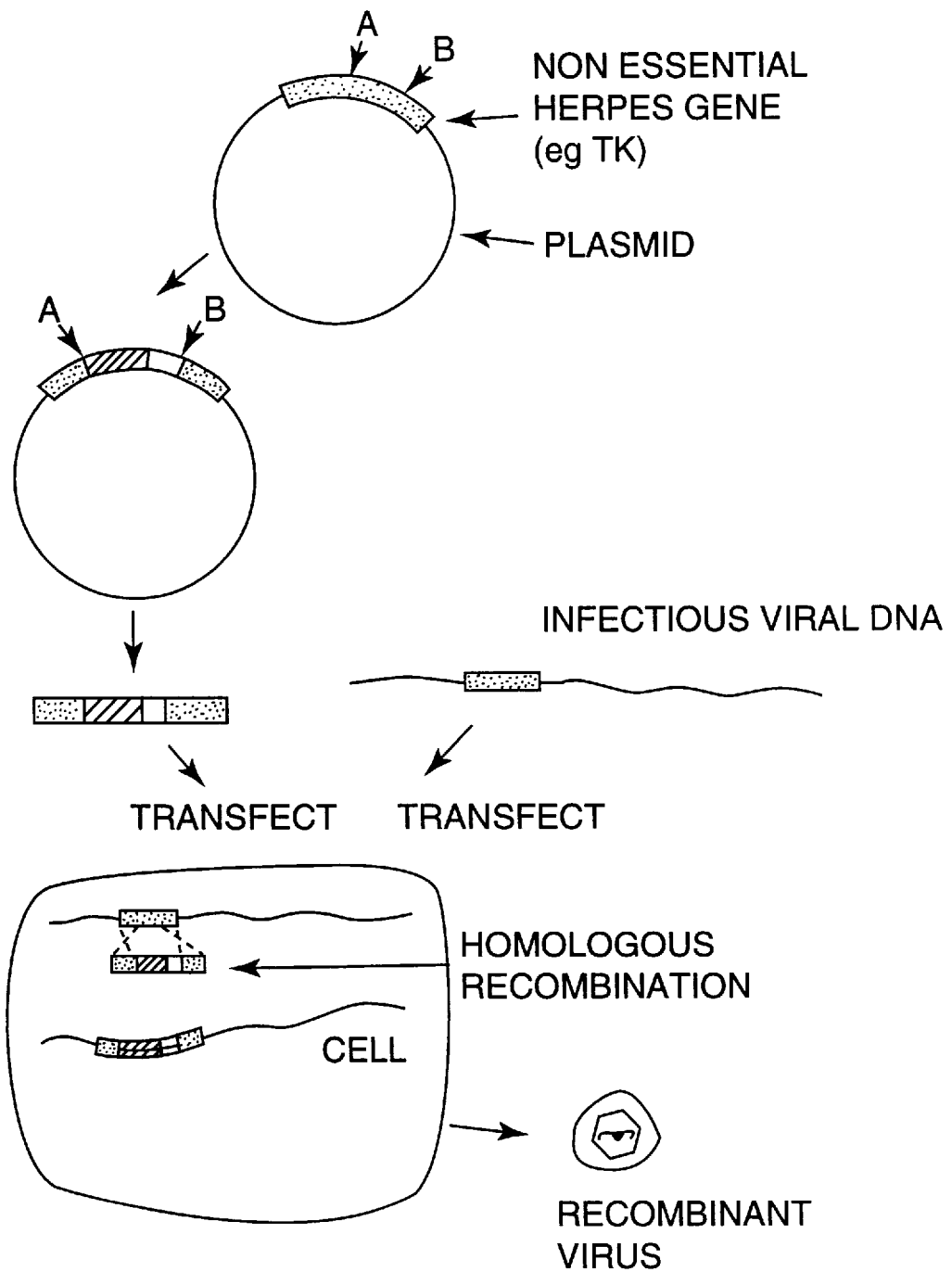

An M13 clone of HVT containing sequences homologous to HSV gH was isolated during our earlier work on gene identification and mapping [Buckmaster et al (1988) as above]. This clone, when used as a probe, hybridized to a 6 Kbp HindIII fragment of HVT (FIG. 3). Sequencing revealed that this fragment contained approximately one quarter of the gH gene including the carboxy terminus. The adjacent HindIII fragment (3.2 Kbp) containing the remainder of the gH gene was identified by hybridization using a cloned HpaI fragment of HVT which overlapped the HindIII site. FIG. 4 shows the sequence of the coding region of the gH gene of HVT (2.3 Kbp) and flanking sequences. The % amino acid identity between the gH gene of HVT and its homologue in HSV1, VZV and EBV was only 20, 24, and 20, respectively (estimated from maximised amino acid overlaps of 630, 644, and 153, respectively).

EXAMPLE 3
TK gene of HVT and TK gene of MDV

Figure 5G:
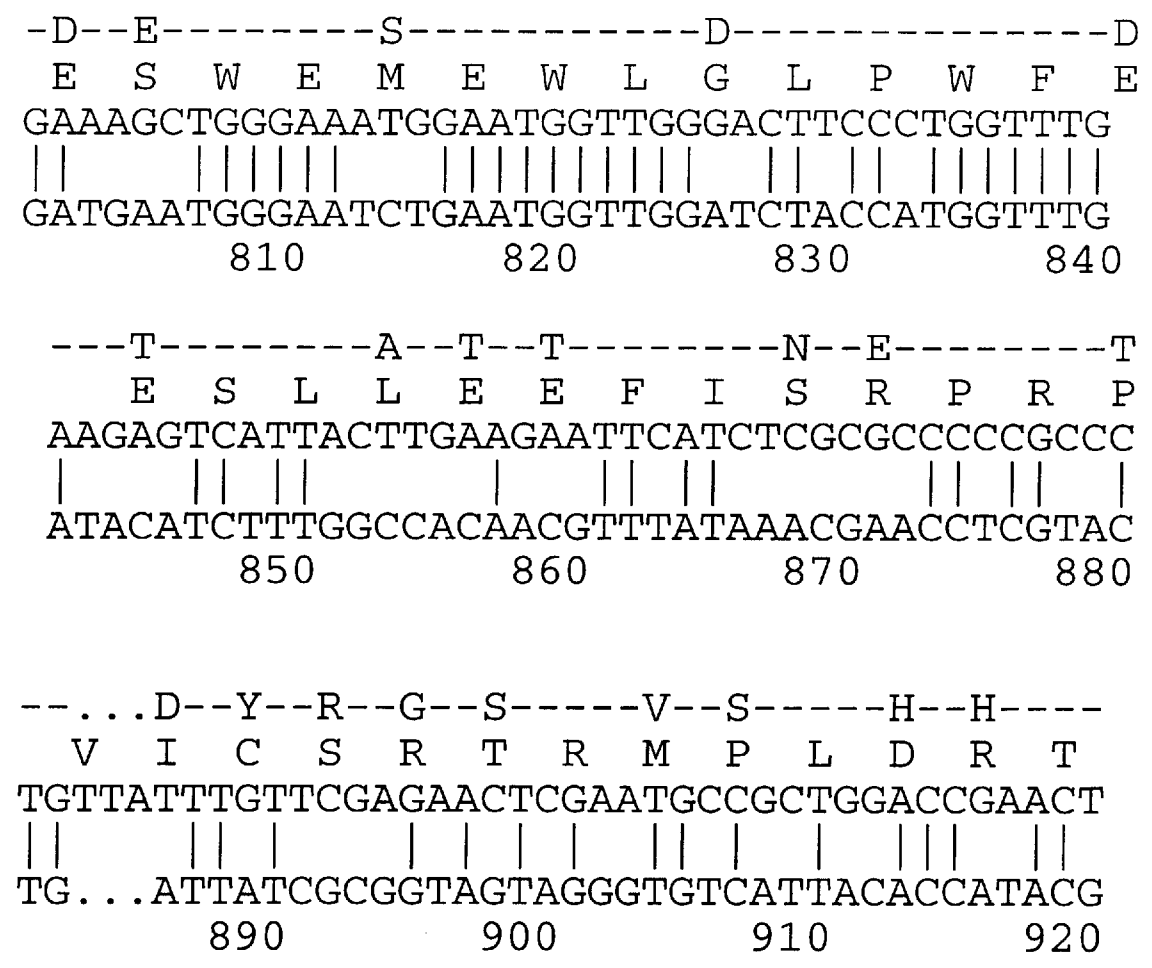
Figure 14A:
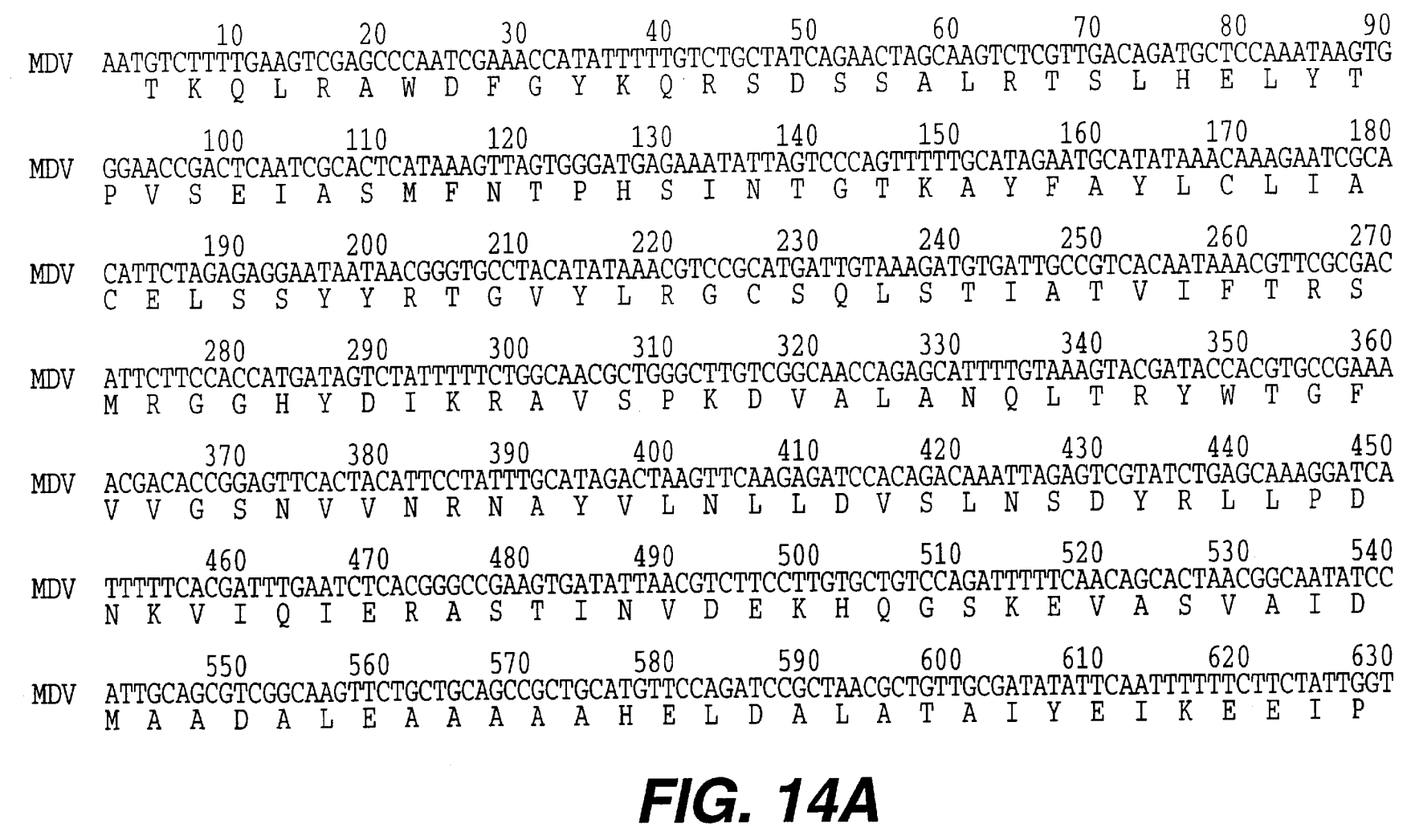
Figure 14B:
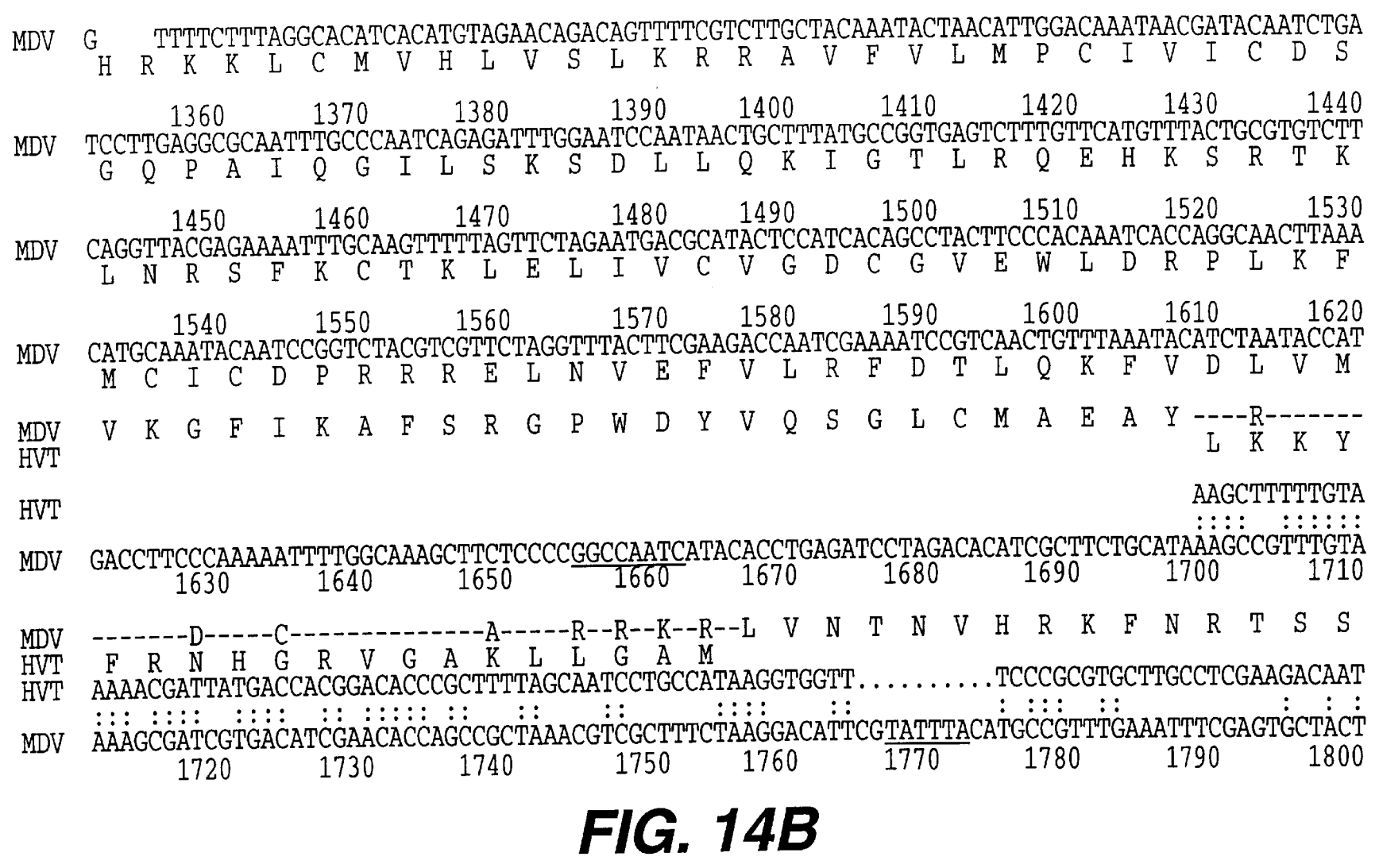
Figure 14B-1:
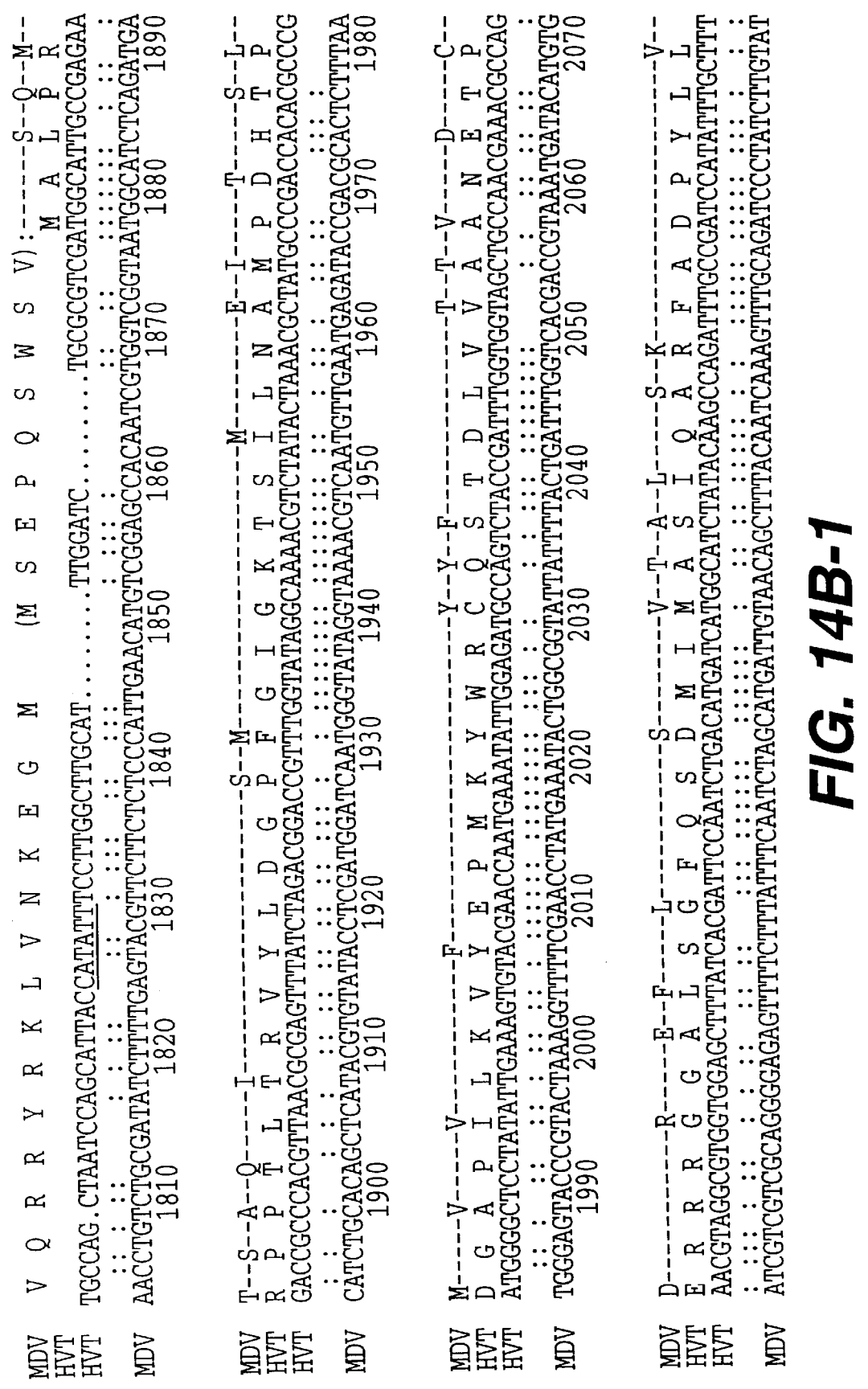
Figure 14C:
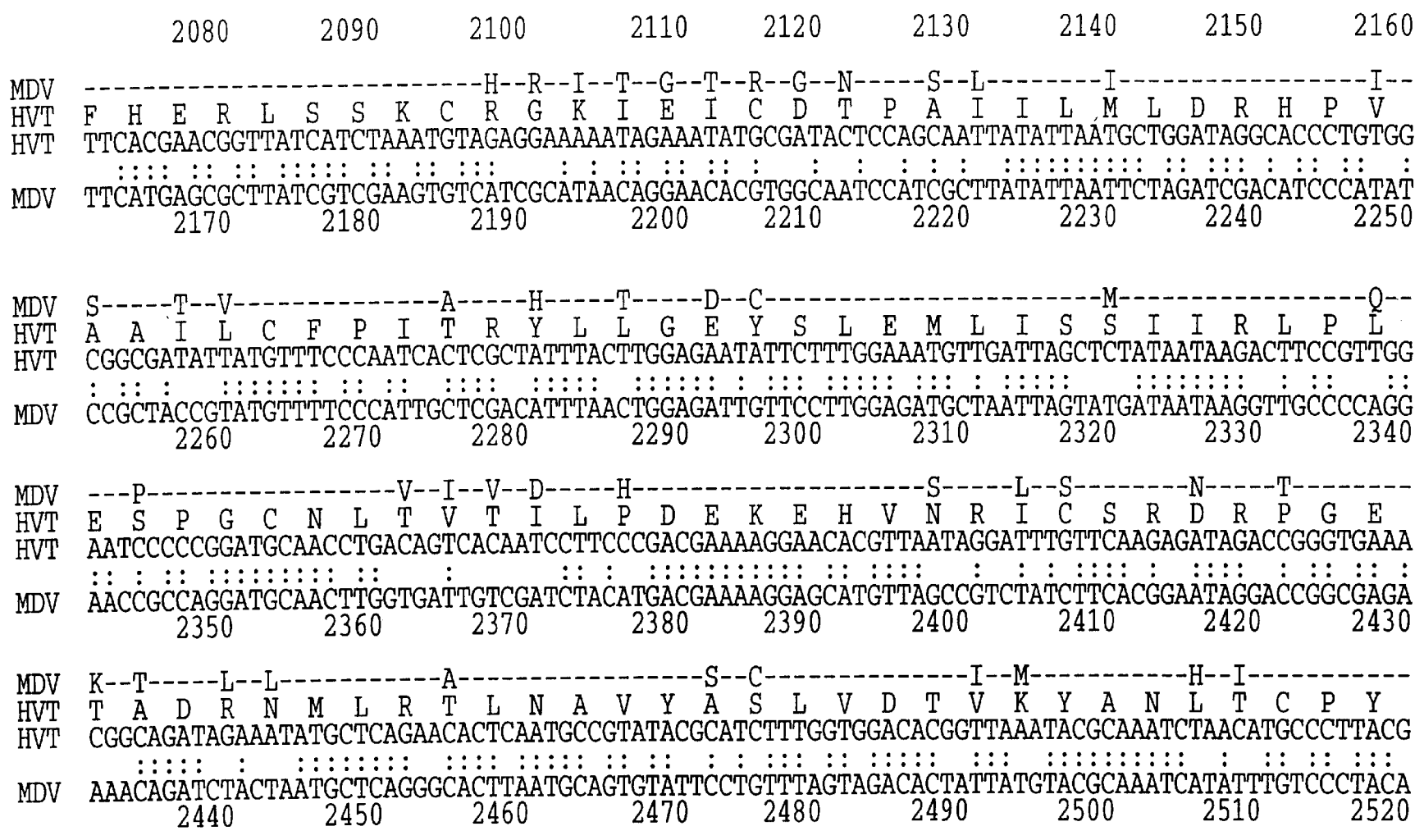
Figure 14C-1:
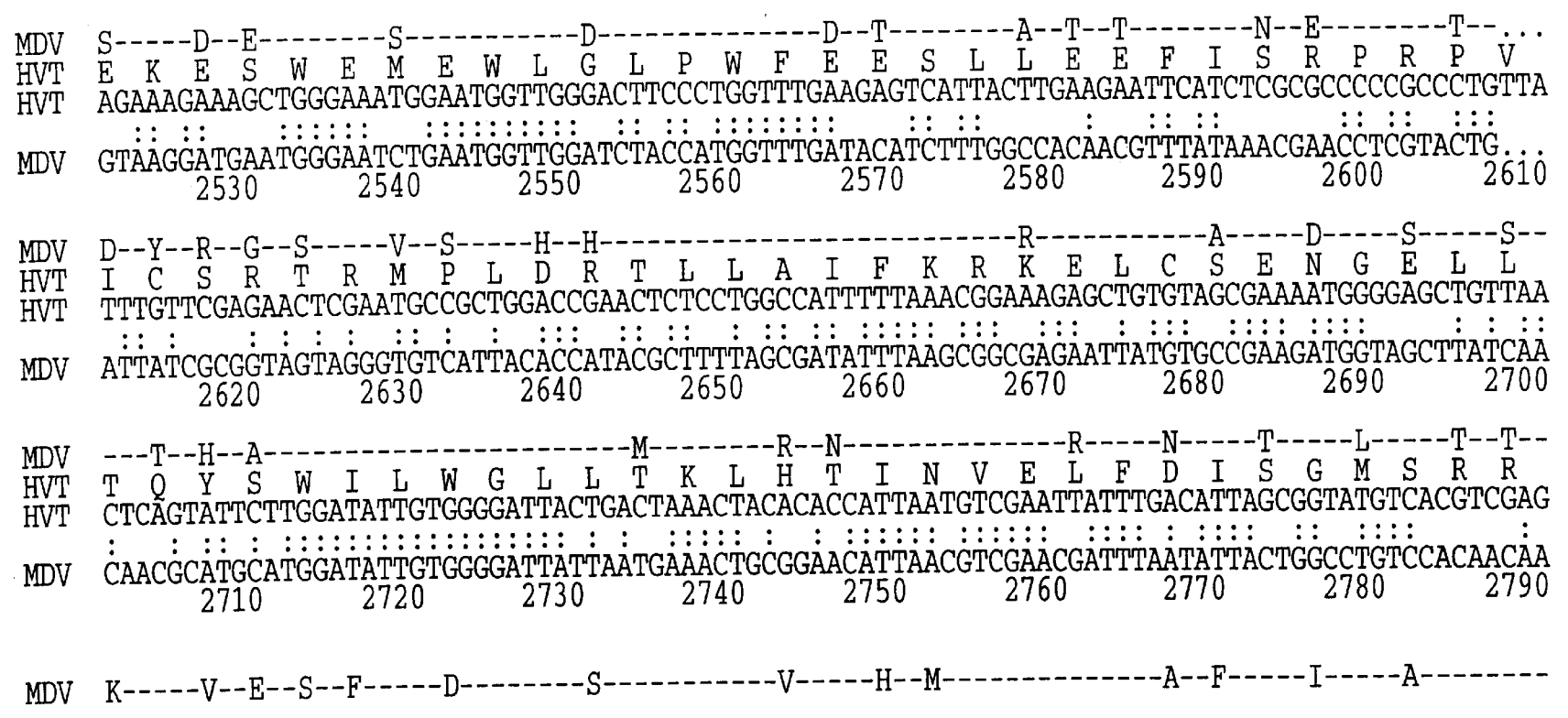
Figure 14D:
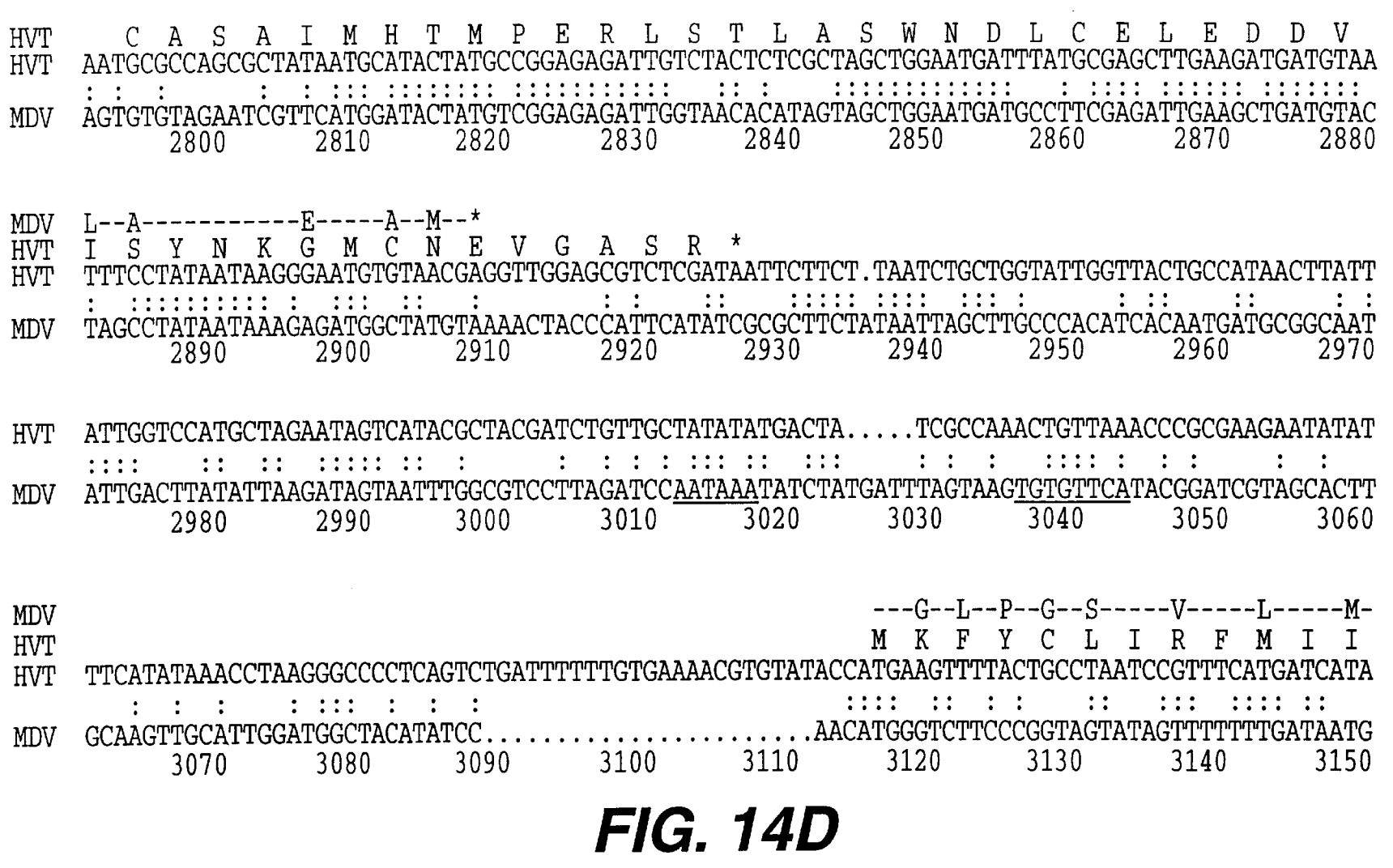
Figure 14D-1:
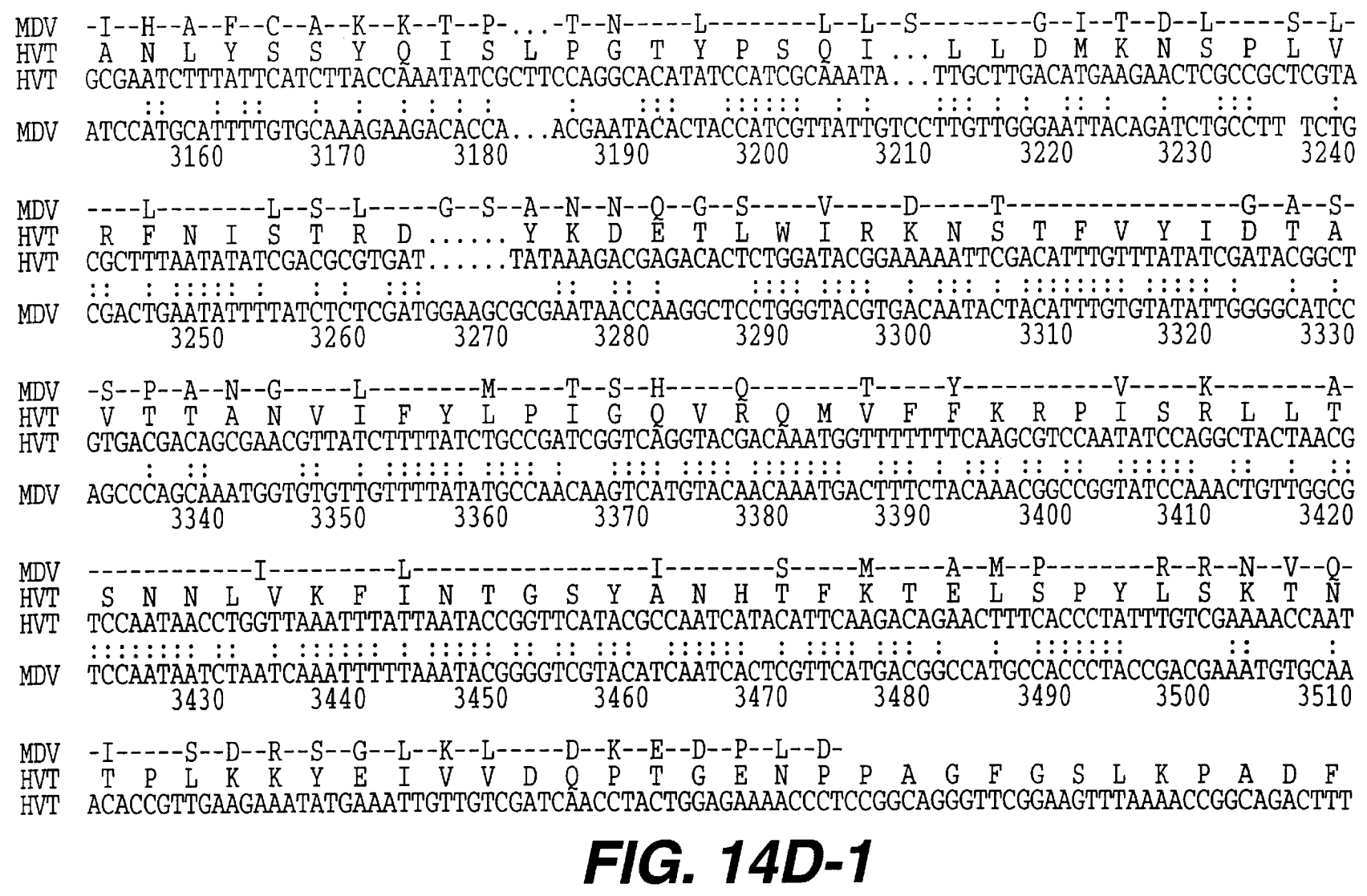
Figure 14E:
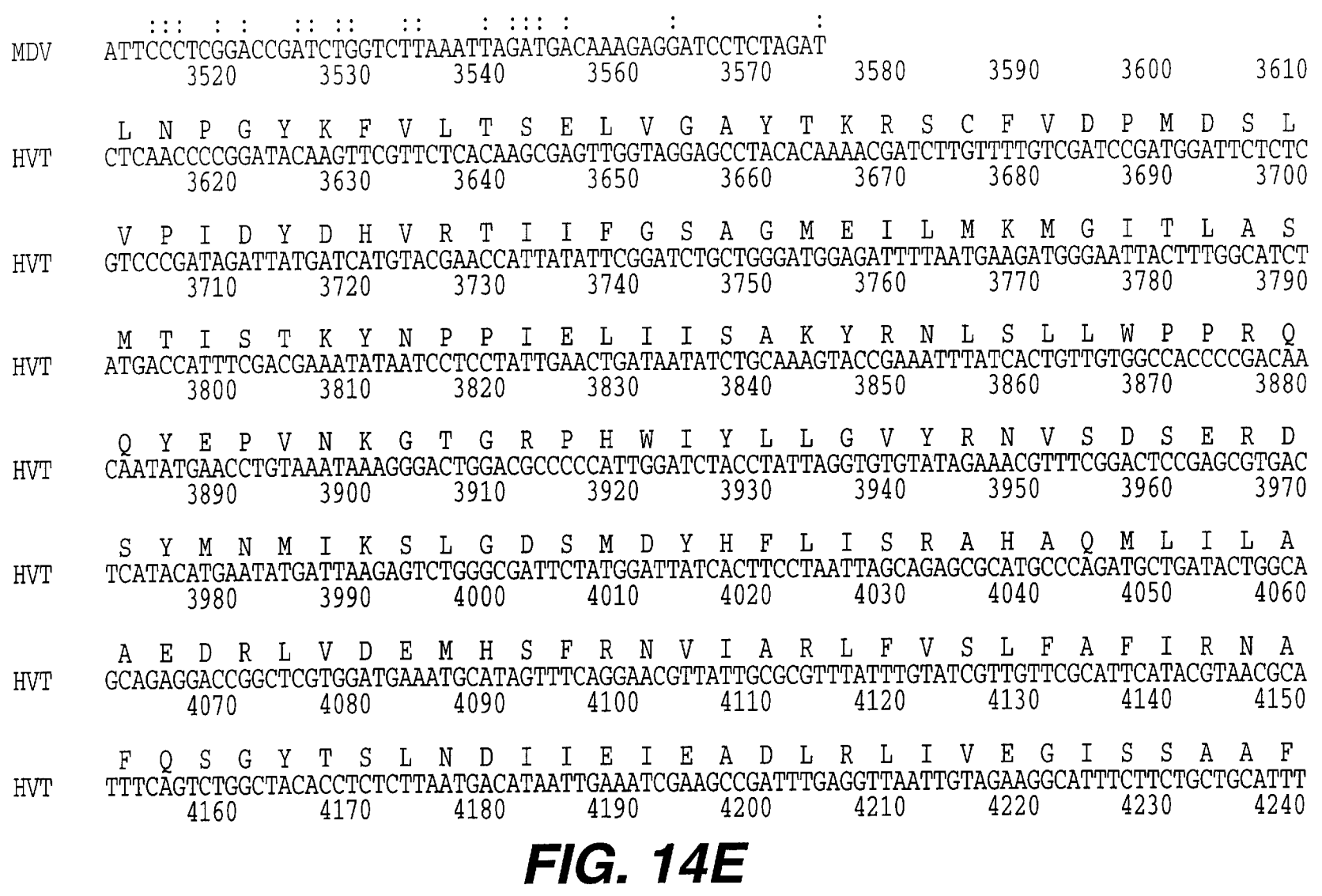

The whole coding region of the TK gene of HVT (1053 bp) was contained within the 3.2 Kbp HindIII fragment described above (FIG. 3). The sequence of the entire gene and flanking regions is shown in FIG. 5. Similarly the whole of the MDV TK gene is contained within the 3.6 Kbp BamHl K2 fragment of MDV (FIG. 1). The complete sequence of MDV TK gene is shown in FIG. 14. Comparison of the MDV and HVT TK sequences shows that the two genes have 60% amino acid identity. By contrast, the % amino acid identities between the TK gene of HVT and the TX genes of HSV 1, VZV, and EBV are only 30, 27, and 24, respectively (estimated from amino acid overlaps of 320, 332, and 193, respectively). The predicted amino acid sequences of HVT and MDV TK show characteristic ATP and/or CTP binding site motifs described for a number of virus and eukaryotic proteins that are associated with phosphorylation [Gentry, G. A. (1985) Proc. Natl. Acad. Sci. U.S.A. 82, 6815–6819]. These conserved sequences are examples of useful sites for insertion and expression of foreign genes and for producing TK– deletion mutants.

EXAMPLE 4
A antigen gene of MDV (gP57–65) (gC homoloque)

The A antigen gene is of interest in vaccine development, both as an immunogen (it encodes a major glycopolypeptide product) and also because we have identified it as the homologue of HSV gC, a potential non-essential region. The A antigen gene was mapped within the BamHI B fragment of MDV (Isfort et al 1987). The MDV GA strain was used. A 2.2 kbp Pvu II-Eco RI fragment was obtained and identified as containing the sequence encoding the A antigen. The nucleotide sequence was determined for the GA strain of MDV [Coussens and Velicer, Abstract OP18.51, VII International Congress of Virology, 9–14 August, (1987) Edmonton, Canada; J. Virol. 62, 2373–2379]. The sequencing work of Coussens et al was made on the same fragement as that identified by Isfort et al. During the random sequencing studies described earlier (Buckmaster et al 1988), we identified an M13 clone (No. 130) which came from the A antigen gene. This clone was then used to identify a 2.3 Kbp EcoR1/PvuII fragment from the RB1B strain of MDV containing the A antigen. This fragment was cloned into a SmaI/EcoRl cleaved pUC13 vector by standard protocols. One plasmid (pMB419) was sequenced by the M13 dideoxynucleotide method. The sequence of the MDV RB1B A antigen and the predicted amino acid sequence of the protein are presented in FIG. 6. The gC gene shown in FIG. 6 is of a very virulent strain of MDV which can be distinguished from the standard MDV isolates such as the MDV GA used by Isfort et al and Coussens et al in that it can cause disease in chickens which are normally genetically resistant to Marek's disease or which have been vaccinated with HVT. Furthermore, a direct comparison between the predicted amino acid sequence of the A antigen encoded by the RBIB strain of MDV and that of the A antigen encoded by the GA strain of MDV showed extensive sequence divergence in the carboxy-terminal region, as well as a variation at the amino terminal of the protein close to the predicted cleavage site of the signal sequence [Binns et al (1989) Virus Research 12, 371–382]. Moreover, as pointed out above, the 3' terminal part of the nucleotide sequence shown in FIG. 6 encodes an anchoring sequence of the gC glycoprotein. Although Coussens et al sequenced the structure of the gC gene, the sequence of the present invention is new, because it is very different from the Coussens et al sequence with respect to the 3' terminal portion. In particular, nucleotides 1408–1500 of Coussens et al differ from nucleotides 1708–1800 of the gC gene of the present invention.

The C-terminal portion of the glycoprotein encoded by the Coussens et al gene differs from the C-terminal portion of the glycoprotein encoded by the gC gene of the present invention. The difference is very important since that region of the gene is crucial for the localization of the glycoprotein gC in the cell after synthesis. The gC encoded by the Coussens et al gene does not contain any anchor sequence with the result that the gC of Coussens et al is secreted into the extracellular medium.

The question of localization was raised by Coussens et al at page 2378, right hand column, second paragraph, wherein it was stated that a carboxyl-terminal membrane anchor sequence is possible. However, the MDV gp57–65 obtained by Coussens et al presented a predominantly secretory nature. Coussens et al therefore concluded that it was not clear whether the small amount of mature gp57–65 is actually anchored in the plasma membrane or held by other interactions.

That point made by Coussens is very important since the presence or absence of anchor sequences makes the glycoprotein totally different in terms of antigen presentation to the cells of the immune system. The gC of the present invention includes the anchor sequence. Thus, gC remains fixed to the membrane, resulting in the presentation of the gC of the present invention.

Figure 16:
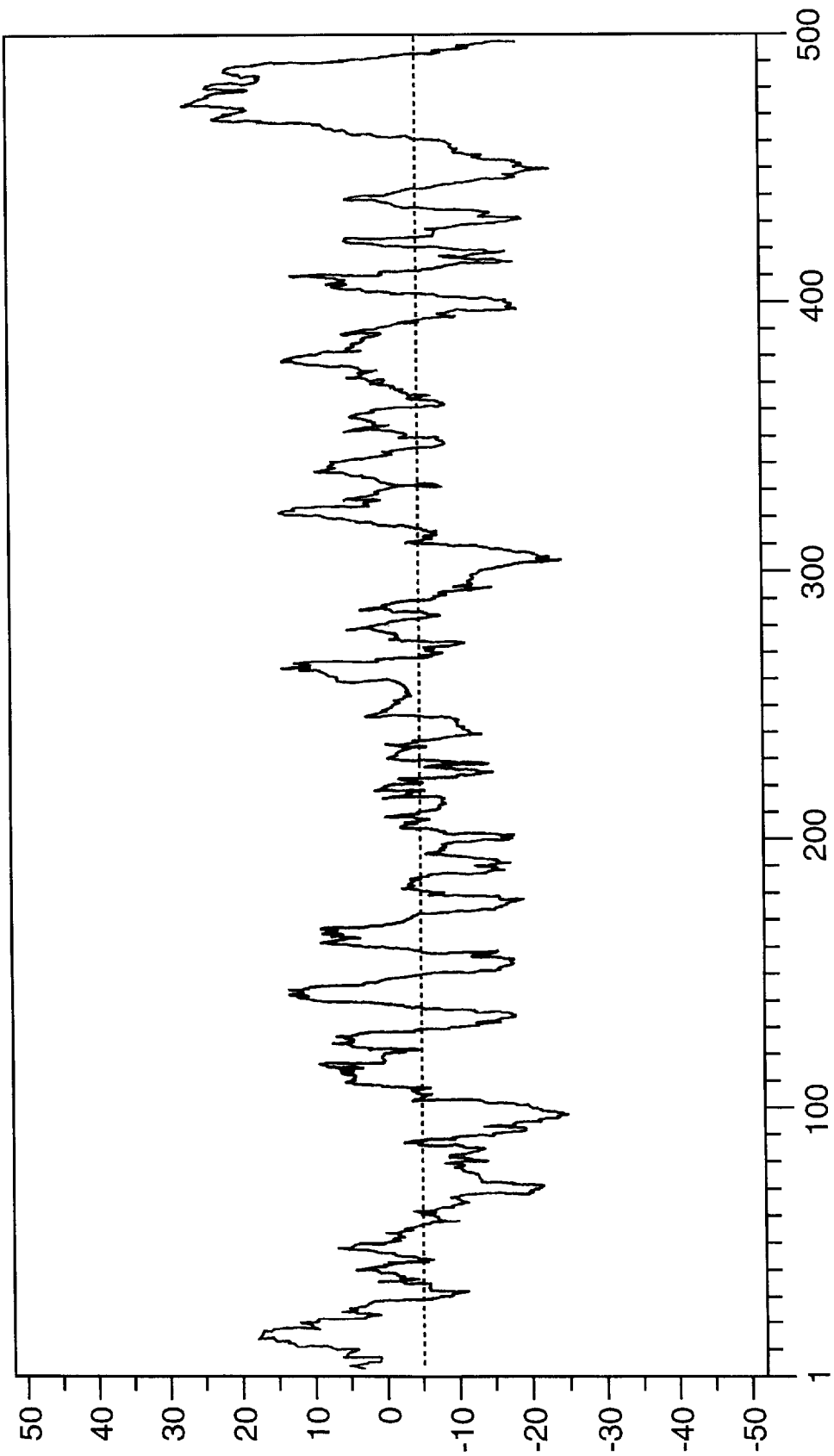
FIG. 16 is a hydropathic index plot of the glycoprotein encoded by the RBIB gC gene.
Figure 17:
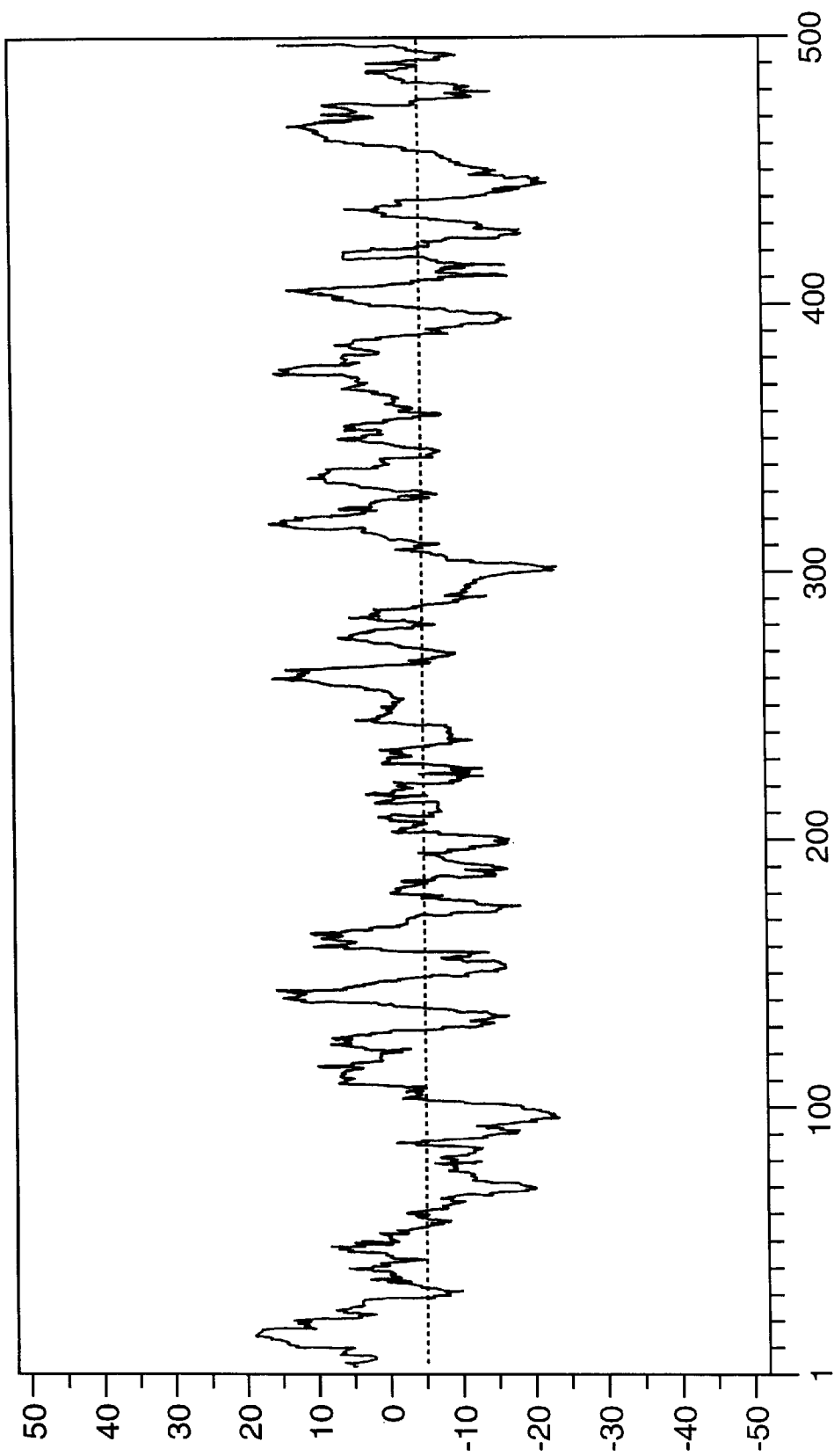
FIG. 17 is a hydropathic index plot of the glycoprotein encoded by the MDV GA A antigen gene.

The absence of an anchor sequence in the gC of Coussens et al has been determined by a study of the hydropathic index from amino acid 1 to amino acid 505 by means of the computer program named SOAP (Intellegenetics PC gene packaged software, Palo Alto, Calif. Also see G. Kyte et al., a drill molecular biology, 1982, 157: 105–132; and P. Kline et al., biochimica biophysica acta 1985, 815: 468–476.) The results of this SOAP study are shown in FIGS. 16 and 17.

As can be seen from a comparison of the hydropathic indices of the gC of Coussens et al (FIG. 17) with the gC of the present invention (FIG. 16), the sequence gC at amino acids 460–500, according to the present invention, is different from the Coussens et al gC sequence, and this difference is crucial as manifested by differences in secretion mode and immunogenicity of the glycoproteins.

The A antigen regions of MDV and HVT are non-essential genes and they can therefore be used as sites in MDV and HVT into which other genes can be inserted into the virus by homologous recombination. Several lines of evidence support this as outlined below.

1) During our study we isolated and sequenced another RB1B A antigen clone. This had one extra T residue in the string of T's 45 bases 3' to the A antigen ATG codon. This extra T would cause a frameshift which would make it impossible for the gene to encode functional A antigen. As it is probable that this gene was cloned from a replicating MDV, the results suggest that the A antigen is non-essential to the virus.

2) On conducting a similarity search it became clear that the MDV A antigen gene is the homologue of HSV gC and PRV gpIII glycoproteins. Both of these homologous genes are known to be non-essential [for the HSV homologue, see Rosenthal et al (1987) J. Virol. 61, 2438–2447].

3) Strains of MDV lacking A antigen as judged by agar gel diffusion tests [Churchill, A. E. et al (1969) J. gen. Virol. 4, 557–564] or producing low levels using the more sensitive 2D radio-immunoprecipitation [van Zaane, D. et al (1982) Virology 121, 133–146] have been reported.

Furthermore, in view of the fact that the A antigen is a major secreted glycoprotein, it may be a particularly suitable location for the presentation of foreign epitopes within the A antigen as soluble, secreted proteins. This may be achieved by cloning oligonucleotides encoding these epitopes in frame within the A antigen gene.

Strategies for Introducing Genes into HVT Vectors

Two possibilities can be envisaged: 1) insertion into non-essential genes of the vector, or 2) substitution of foreign gene for corresponding gene of the vector. This would be possible only in regions which already have substantial homology as may be the case between some genes of MDV and HVT.

EXAMPLE 5

Insertion into non-essential genes of HVT or MDV (a) Insertion at the TX locus of the vector.

1) HVT or MDV may be used as vectors for insertion and expression of avian herpesvirus genes. In particular gB, gH or gC of RB1B MDV may be inserted into HVT. One may use the promoter associated with the inserted gene or use heterologous promoters, including those of a different class of genes (for example, the immediate early promoter to optimize expression of gB).

2) HVT or MDV may be used as general vectors for the insertion and expression of genes unrelated to avian herpes viruses and likely to require manipulation of promoters for optimal expression. The procedure to be used for gene insertion is substantially as described previously for the insertion of hepatitis antigen in HSV [Shih et al, 1984 as above].

MDV and HVT DNA, obtained as described above, is infectious provided that precautions are taken not to shear the DNA during extraction. Calcium phosphate precipitates of viral DNA prepared as described by Stow and Wilkie [(1976) J. gen. Virol. 33, 477] were added to sub-confluent monolayers of CEF. After absorption for 1 h at 37° C., culture medium was added and cultures were incubated for 1 or 2 days until confluent. Monolayers were then trypsinized, replated (1:1 or 1:2) in 199 medium (Wellcome) containing 2 to 4% calf serum, and incubated at 37° C. until plaques developed, usually after 4 to 5 days. Approximately 200 plaques may be obtained per $\mu$g of HVT DNA and approximately 50 per $\mu$g of MDV DNA.

For homologous recombination and isolation of recombinant virus, genes of interest are inserted within non-essential genes such as TK or gC and co-transfected with wild-type viral DNA at molar ratios ranging from 10:1 to 2:1, as described above. Alternatively, intact wild-type virus may be used for co-infection.

Restriction enzyme sites that could be used for the insertion of foreign antigens into the TK of HVT strain Fc-126 include: BanII, Bspl286, DraIII, EcoRl, HincII, HpaI, NheI and, NspbII.

RE sites that could be used to produce defined TK deletion mutants in MDV serotype I strain RE13 include; BalI, Haell, NdeI and SphI as insertion sites for foreign DNA that would disrupt the TK gene, and double digests of combinations of these four restriction enzymes (EcoK could also be used) to remove a portion of the TK gene, thus inactivating it.

Some of these enzymes also have sites in the plasmid vector into which the virus DNA fragments are cloned. Thus, in order to linearize the clone DNA without also cutting within the vector, partial digests may be carried out.

None of the above enzymes should cause any disruption to flanking genes, HSV-1 homologues of which are known to play an important role in virus multiplication.

Virus recombination may be detected by 'plaque lifts', which involve transfer of infected cells and released virus which have adhered to the agar overlay to nitrocellulose and hybridization of the denatured DNA released from the cells and virus to suitable probes as described by Villareal, L. et al [(1977) Science 196, 183–185]. Virus which hybridizes to the probe may be recovered from the monolayer.

A similar procedure may be used to isolate recombinant virus which expressed epitopes of interest. In this instance the nitrocellulose "plaque lifts" are treated with antibody and the presence of bound antibody revealed using a suitable detection system, such as labelled protein A or phosphatase-conjugated antiglobulin antibody.

The gene of interest with appropriate promoters is first inserted within the cloned TK gene. The recombinant DNA is then co-transfected with infectious DNA of the vector in chick embryo fibroblasts or chicken kidney cells and TK− virus may be selected by growth in medium containing acyclovir [Ross, N. (1985) as above] or FMAU [Schat, K. A. et al (1984) Antiviral Research 4, 159–270]. Alternatively, or in addition, plaques are screened for the presence of the gene of interest using 'plaque lifts' on nitrocellulose and hybridization to any relevant labelled probe. Plaques are also screened for expression of the epitopes of interest using monoclonal antibodies or antipeptide antibodies.

The main advantage of this strategy is that the selection procedure increases the chances of obtaining virus recombinants containing the gene of interest. It also offers the opportunity of using different promoters for optimum expression. Thus, the use of an immediate early promoter may allow expression in latently infected cells.

(b) Insertion at other non-essential sites of the vector. Since the A antigen (HVT and MDV homologues of HSV gC) is not essential for virus growth in vivo and in vitro (see section on gC above) it is a potentially useful site for the insertion and expression of foreign genes. Moreover, since it is one of the most abundant antigens and is excreted, it may be particularly useful for enhancing the immunogenic properties of foreign proteins. The isolation of virus recombinants at this locus may be achieved by first inserting at least part of the gene of interest in frame within the gC gene and then co-transfecting with infectious viral DNA. Screening of virus plaques with sequence specific probes or with specific antibody allows the isolation of recombinants.

An antigen-encoding sequence can also be inserted into the ribonucleotide reductase (large subunit) gene of HVT or of MDV—see FIGS. 8 and 9.

EXAMPLE 6
Substitution of MDV genes for their homologues in HVT

Substitution may be achieved by co-transfection of cloned MDV sequences and infectious HVT DNA as described in Example 5. Substitution of the gB and gC genes derived from the RB1B strain of MDV for their counterparts in HVT may be effected as may substitution of the gH gene of MDV, other glycoproteins, and immediate early genes.

Recombinants expressing MDV sequences and epitopes may be detected using MDV-specific monoclonal antibodies or anti- peptide anti-bodies raised against unique MDV sequences as described above.

The advantage of this procedure is that it is relatively simple and does not require manipulation of promoters. However, it may be limited to genes which share substantial homology.

EXAMPLE 7
Strategies for obtaining TK- mutants of MDV Deletion mutants.

Deletions may be introduced within any suitable part of the gene, for example, the domains of the gene that are required for nucleoside binding. This may be achieved by restriction enzyme double digestion, for example, with HaeII and any of the following enzymes: BaiI, NdeI, SphI or EcoK. Appropriate fragments are then relegated, followed by co-transfection with infectious viral DNA or transfection into virally-infected cells. Reference may be made to FIGS. 7 and 8, and to the section above relating to insertion of heterologous sequences, in choosing restriction enzymes and so on. TK- virus may be selected in the presence of acyclovir [Ross, N. (1985) as above] or FMAU [Schat, K. A. et al (1984) as above]. Plaque-purified clones may then be tested for the absence of the deleted portion of the TK gene by hybridization.

The deletion mutants of MDV may be used themselves as attenuated viruses for vaccine preparation, or may have sequences for heterologous antigens inserted.

Insertional mutants.

A functional β-galactosidase gene under the control of a herpesvirus promoter, or any other suitable sequence, or a single base is first introduced in a domain of the TK gene which is essential for TK activity. The recombinant DNA is then co-transfected with infectious viral DNA or transfected into virally-infected cells to allow homologous recombination to occur. Selection in the presence of acylovir or FMAU will yield TK- insertional mutants. If a β-galactosidase gene is introduced, mutants can be detected by the production of blue plaques in the presence of X-gal.

The TK gene and surrounding sequences may be subcloned into another suitable vector, if necessary.

EXAMPLE 8
Insertion of MDV RB1B gB gene into HVT

The HVT TK gene is cloned in the plasmid vector pUC13 to generate a plasmid, which is termed pTXlB. This plasmid is linearised with, for example, the restriction endonuclease RsrII which cleaves the plasmid only within the TK gene (nucleotide position 197 in FIG. 5, enzyme recognition sequence CGGACCG). The "sticky" ends thus generated can be end repaired by standard techniques (see "Molecular Cloning: a Laboratory Manual", ed. Maniatis T., Fritsch E. F., and Sambrook J. Cold Spring Harbor Laboratory 1982).

The RB1B gB was originally cloned on two plasmids which may be termed RB1B-BamHl-$I_3$ and RB1B-BamHI-$K_3$. (Note $I_3$ had lost one BamHl site during cloning.) To generate a complete gB copy on one plasmid, both plasmids were cleaved with BamHl and the fragments ligated. Recombinants containing the desired configuration were identified by restriction enzyme analysis of plasmid DNA'S. However, as described above, the complete gB sequence was subsequently obtained on an EcoRI/SalI fragment.

Further information regarding the sequence encoding MDV gB and its manipulation may be found in Ross et al [J. gen. Virol (1989) 70 1789–1804].

The single recombinant plasmid of Ross et al is then cleaved with EcoRI and SalI, the ends are repaired, and the plasmid is cloned into PTK1B prepared as above. Alternatively, the MDV gB open reading frame could be excised from plasmid MSB27 by digestion with HincII and NaeI and the products ligated to HVT TK plasmid pTKlB, cleaved partially with HpaI. Recombinant plasmids containing both TK and gB sequences could be identified by hyrbridization and further characterized by Southern blotting. The recombinant plasmids are then introduced into cells containing HVT virus (viral DNA) and homologous recombination will introduce the gB gene into the TK gene. HVT viral recombinants can be selected with acyclovir or FMAU or alternatively detected with labelled gB probes.

EXAMPLE 9
RB1B gC (A antigen) gene into HVT

Blunt ended PTK13 is prepared as in Example 8. The RB1B gC is cleaved from the plasmid pMB419 (Example 4) with the restriction endonucleases EcoR1 and HindIII (site within the pUC13 polylinker). The sticky ends generated are again end-repaired by standard protocols. The end-repaired gC fragment is then cloned into the linearized end-repaired pTXlB as in Example 8. (The cloning can be verified by analysis of the resulting clones with restriction enzymes, probing with radioactively labelled fragments, or DNA sequencing, or any combination of these).

The resulting plasmid with the RB1B gC gene cloned into the HVT TK gene can then be introduced into the HVT genome by transfecting the plasmid into HVT-infected cells using calcium phosphate precipitation or electroporation. Homologous recombination, involving cross-overs either side of the gC gene, between the HVT virus and the flanking sequences of the HVT TK plasmid will carry the RB1B gC gene into the HVT viral genome. Viral recombinants can be selected for (as they are TK–) or identified (e.g. by probing) as described above.

In analogous ways, the sequence information given above and in the Figures can be used to design cloning strategies for the insertion of these genes and others into the non-essential genes of the HVT described here or to generate combinations of antigen genes in HVT.

EXAMPLE 10
MDV gD gene

FIG. 15 shows part of the sequence of the MDV gD gene. The sequence was obtained by sequencing random fragments of the $U_s$ region MDV DNA and comparing the sequence to the sequence of known herpesvirus genes (see Buckmaster et al, loc. cit.). The sequence gave homology scores of 189 and 216, respectively, with HSV gD and PRV gp50. The sequence information assists in the preparation of suitable probes to isolate and characterize the gene.

What is claimed is:

1. A nucleotide sequence having the sequence of the coding portion of the MDV gB gene, as set forth in FIGS. 2A to 2R.

2. A nucleotide sequence consisting of the nucleotide sequence of claim 1 and at least part of the 5' non-coding portion of said sequence.

3. A nucleotide sequence consisting of the nucleotide sequence of claim 1 and at least part of the 3' non-coding portion of said sequence.

4. A plasmid comprising the nucleotide sequence of claim 1.

* * * * *